US011619059B2

(12) United States Patent
Witelson et al.

(10) Patent No.: US 11,619,059 B2
(45) Date of Patent: Apr. 4, 2023

(54) MULTI PARAMETER SWIMMING POOL FLUID ANALYSIS AND REGULATING METHOD AND DEVICE

(71) Applicant: Maytronics Ltd., Kibbutz Yizrael (IL)

(72) Inventors: Shay Witelson, Kibbutz Yizrael (IL); Tamir Yizhack, Kiryat Motskin (IL); Shay Peretz, Shimshit (IL); Gil Hilel, Kibbutz Yizrael (IL)

(73) Assignee: MAYTRONICS LTD., Kibbutz Yizrael (IL)

( * ) Notice: Subject to any disclaimer, the term of this patent is extended or adjusted under 35 U.S.C. 154(b) by 1289 days.

(21) Appl. No.: 15/761,133

(22) PCT Filed: Sep. 20, 2016

(86) PCT No.: PCT/IL2016/051037
§ 371 (c)(1),
(2) Date: Mar. 19, 2018

(87) PCT Pub. No.: WO2017/046808
PCT Pub. Date: Mar. 23, 2017

(65) Prior Publication Data
US 2018/0266131 A1    Sep. 20, 2018

Related U.S. Application Data

(60) Provisional application No. 62/221,029, filed on Sep. 20, 2015.

(51) Int. Cl.
*E04H 4/12*       (2006.01)
*E04H 4/16*       (2006.01)
(Continued)

(52) U.S. Cl.
CPC ......... *E04H 4/1209* (2013.01); *E04H 4/1654* (2013.01); *G01N 21/255* (2013.01);
(Continued)

(58) Field of Classification Search
CPC .............. E04H 4/1209; E04H 4/1654; G01N 33/1886; G01N 21/31; G01N 21/645;
(Continued)

(56) References Cited

U.S. PATENT DOCUMENTS

2004/0149663 A1    8/2004  Nakanishi et al.
2007/0092406 A1    4/2007  Ben David
(Continued)

FOREIGN PATENT DOCUMENTS

CN    202808453    3/2013
CN    105372194    3/2016
(Continued)

OTHER PUBLICATIONS

Submersible Spectrofluorometer for Real-Time Sensing of Water Quality (may be viewed at: http://www.mdpi.com/1424-8220/15/6/14415/htm) Adriana Puiu; Luca Fiorani; Ivano Menicucci; Marco Pistilli; Antonia Lai 18 Jtm 2015 (Jun. 18, 2015) abstract, sections 2.1, 2.2, 2.4.
Monitoring organic loading to swimming pools by fluorescence excitation-emission matrix with parallel factor analysis (PARAFAC) Seredy?ska-Sobecka B; Stedmon CA; Boe-Hansen R; Waul CK; Arvin E Mar. 31, 2011 (Mar. 31, 2011) abstract.

*Primary Examiner* — Fred Prince
(74) *Attorney, Agent, or Firm* — Reches Patents

(57) ABSTRACT

A pool maintenance system that includes a spectroscopic device that is configured to analyze a fluid of a pool.

22 Claims, 18 Drawing Sheets

(51) Int. Cl.
*G01N 33/18* (2006.01)
*G01N 21/31* (2006.01)
*G01N 21/64* (2006.01)
*G01N 21/25* (2006.01)
*G01N 21/85* (2006.01)

(52) U.S. Cl.
CPC ........... *G01N 21/31* (2013.01); *G01N 21/645* (2013.01); *G01N 33/182* (2013.01); *G01N 33/1826* (2013.01); *G01N 33/1886* (2013.01); *G01N 21/85* (2013.01); *G01N 2021/6491* (2013.01); *G01N 2201/0218* (2013.01)

(58) Field of Classification Search
CPC ............... G01N 21/255; G01N 33/182; G01N 33/1826; G01N 2021/6491; G01N 2201/0218; G01N 21/85
USPC ...... 210/167.1, 167.11, 167.16, 167.17, 143, 210/739, 742, 743, 745; 15/1.7
See application file for complete search history.

(56) References Cited

U.S. PATENT DOCUMENTS

| | | |
|---|---|---|
| 2013/0134104 A1 | 5/2013 | Forstmeier et al. |
| 2015/0166361 A1 | 6/2015 | Fischmann |
| 2016/0244988 A1* | 8/2016 | Barcelos ............. G05D 1/0242 |
| 2017/0215261 A1* | 7/2017 | Potucek ............. F04D 15/0281 |
| 2017/0248568 A1* | 8/2017 | Yizhack ................. G01N 21/33 |
| 2017/0275905 A1* | 9/2017 | Liu ..................... A61H 33/0087 |
| 2018/0305948 A1* | 10/2018 | Lection ................... C02F 1/001 |
| 2021/0147255 A1* | 5/2021 | Burnham ........... G01N 33/1886 |

FOREIGN PATENT DOCUMENTS

| | | |
|---|---|---|
| DE | 19515428 | 11/1996 |
| EP | 0201824 | 11/1986 |
| EP | 2058282 | 5/2009 |
| FR | 2907551 | 4/2008 |
| WO | 03046549 | 6/2005 |
| WO | 2010146110 | 12/2010 |
| WO | 2016046719 | 3/2016 |

\* cited by examiner

MULTI PARAMETER SWIMMING POOL FLUID ANALYSIS AND REGULATING METHOD AND DEVICE

CROSS REFERENCE TO RELATED APPLICATIONS

This application claims priority from U.S. provisional patent Ser. No. 62/221,029 filing date Sep. 20, 2015, which is incorporated herein by reference.

FIELD OF THE INVENTION

This invention relates to pool fluid analysis and fluid treatment devices.

BACKGROUND OF THE INVENTION

The pool industry is divided into two main classes. The first is the public pool sector that may be defined by pool sizes, volumes of fluid contained and the fact that these may be business or commercially oriented pool owners. It may also be defined by the number of visitors and users to such a pool. i.e.: it is not uncommon to see a small/medium sized public pool with a size of say 12 m×6 m that accommodates a large number of swimmers. This group may also comprise of 50 meters long Olympic pools, large hotel pools, hostels, caravan park pools, large recreational pools but also smaller community pools that may all need to comply with strict public health regulations governing this sector in their respective countries or municipalities.

The second and possibly the larger pool sector includes the privately owned pools that may usually be smaller in sizes, in their fluid volumes and in number of swimmers. Such pools may not always need to comply with strict fluid quality regulations.

The public pools sector is usually compelled to install expensive fluid quality equipment systems whilst the private sector is not compelled to invest heavily into such equipment but nevertheless, many private pool owners want their pools to be treated to be hygienic and clean.

Fluid treatment in general has the aim of maintaining fluid quality parameters on a continuous basis. This process is based on sampling, sensing, analyzing and appropriately responding to results of analysis.

Preventive pool water analysis and subsequent measures has a major effect on the time and cost required to maintain hygienic water characteristics by dispensing economical and safe chemicals at the right time.

Preventive measures may include, for analysis and warning about hygiene level deviations, the use of a pool maintenance systems that are available in the market.

There is a growing need to provide cost effective pool fluid monitoring systems and methods.

SUMMARY

According to an embodiment of the invention there may be provided a pool maintenance system (also referred to as system) that may include a spectroscopic device; wherein the spectroscopic device may be configured to analyze a fluid of a pool.

According to an embodiment of the invention there may be provided a method for analyzing a fluid of a pool, the method may include analyzing the pool fluid by a spectroscopic device.

According to an embodiment of the invention the fluid of the pool may be analyzed by multiple spectroscopic devices. Different spectroscopic devices may analyze the same spectrum or may analyze different spectrums.

There may provided a pool maintenance system that may include a spectroscopic device; wherein the spectroscopic device may be configured to analyze a fluid of a pool.

The spectroscopic device may be configured to analyze the fluid of the pool by applying fluorescence spectroscopy and absorbance spectroscopy.

The pool maintenance system may be a pool cleaning robot, a skimmer, a pool maintenance system that may be coupled to a pool filtering system, a pool maintenance system that may be included in a pool filtering system, a pool maintenance system that may be mechanically coupled to the pool, a partly submerged motorized water surface skimming system and a pool maintenance free floating system that may be at least partially submerged in the fluid of the pool when the pool may be at least partially filled with the fluid of the pool.

The spectroscopic device may include multiple radiation sources for illuminating a sample of the fluid of the pool with multiple radiation beams from different directions; at least one sensor; and collection optics for directing, to the at least one sensor, one or more radiation beams out of a passed through radiation beam that passes through the sample and a reflected radiation beam that was reflected from the sample.

The collection optics may be configured to direct to the at least one sensor the passed through radiation beam and the reflected radiation beam at the same point in time.

The collection optics may be configured to direct to the at least one sensor the passed through radiation beam and the reflected radiation beam at different points in time.

The collection optics may be configured to direct to a first sensor of the at least one sensor the passed through radiation beam and to direct to a second sensor of the at least one sensor the reflected radiation beam.

The at least two of the multiple radiation beams may be perpendicular to each other.

The multiple radiation sources may be configured to illuminate the sample with the multiple radiation beams at different points of time.

The multiple radiation sources may be configured to illuminate the sample with the multiple radiation beams simultaneously.

The multiple radiation sources may include at least two radiation sources out of an ultraviolet source, a visible light source and a near infrared source.

The multiple radiation sources may include an ultraviolet source, a visible light source and a near infrared source.

The multiple radiation sources may include a dual frequency range radiation source and single radiation range radiation source; wherein the dual frequency radiation source may be configured to generate radiation within two frequency ranges out of ultraviolet, near infrared and visible light; wherein the single radiation range radiation source may be configured to generate radiation within a single frequency range out of ultraviolet, near infrared and visible light.

The multiple radiation sources may include a first dual frequency range radiation source that has a first optical axis and a second dual frequency radiation range source that has a second optical axis; wherein the first and second optical axes may be oriented to each other; wherein each dual frequency radiation source may be configured to generate radiation within two frequency ranges out of ultraviolet, near infrared and visible light.

The first and second dual frequency range radiation sources may be configured to generate, at a same point of time, radiation beams that differ from each other by frequency.

The at a first point in time the collection optics may be configured to direct towards the at least one sensor a passed through radiation beam of a first frequency range that passes through the sample and a reflected radiation beam of a second radiation range that was reflected from the sample.

The spectroscopic device may include a single radiation source for illuminating a sample of the fluid of the pool with a radiation beam; at least one sensor; and collection optics for directing, to the at least one sensor, one or more radiation beams out of a passed through radiation beam that passes through the sample and a reflected radiation beam that was reflected from the sample.

The pool maintenance system may include a controller that may be configured to automatically determine when to apply fluorescence spectroscopy and when to apply absorbance spectroscopy.

The spectroscopic device may be waterproof and at least a portion of the spectroscopic device may be configured to contact the fluid of the pool.

The spectroscopic device may be waterproof.

The pool maintenance system wherein the pool maintenance system may be configured to control water quality and hygiene parameters of the pool water.

The pool maintenance system wherein the spectroscopic device may be configured to analyze the fluid of the pool to provide information about levels of organic and inorganic materials in the pool.

The pool maintenance system may be a pool cleaning robot; wherein the pool cleaning robot may include a sensor for sensing a status of the pool cleaning robot; and a controller; wherein the controller may be configured to control a movement of the pool cleaning robot based on a status of the pool cleaning robot as sensed by the sensor and based on one or more scheduled analysis of the fluid of the pool by the spectroscopic device.

The status of the pool cleaning robot may be selected out of a speed of propagation of the pool cleaning robot, an inclination of the pool cleaning robot, an acceleration of the pool cleaning robot, and vibrations of the pool cleaning robot.

The sensor may be a vibration sensor that may be configured to sense vibrations of the pool cleaning robot; wherein the controller may be configured to facilitate an analysis of the fluid of the pool only when the vibrations of the pool maintenance system may be below a vibrations threshold.

The sensor may be a speed sensor that may be configured to sense a speed of propagation of the pool cleaning robot; and wherein the controller may be configured to control a reduction of a speed of propagation of pool cleaning robot to be below a speed threshold during an analysis of the fluid of the pool.

The sensor may be a vibration sensor that may be configured to sense vibrations of the pool cleaning robot; and wherein the controller may be configured to control a reduction of a vibration of propagation of pool cleaning robot to be below a vibration threshold during an analysis of the fluid of the pool.

The pool maintenance system may include a controller that may be configured to receive from the spectroscopic device a result of an analysis of the fluid of the pool and to schedule, based on the result, another analysis of the fluid of the pool.

The pool maintenance system may be a pool cleaning robot that may include a controller that may be configured to schedule multiple analyses of the fluid of the pool at different locations within the pool.

The at least two locations of the different locations may be positioned at different distances from a bottom of the pool.

The one location of the different locations may be at a bottom of the pool and another location of the different positioned may be at a surface of the fluid.

The pool cleaning robot may be positioned at a first orientation when located at a first location of the different locations; and wherein the pool cleaning robot may be positioned at a second orientation when located at a second location of the different locations; wherein the first orientation differs from the second orientation.

The pool maintenance system may include a controller that may be configured to receive a schedule of multiple analyses of the fluid of the pool and modify the schedule based on at least one result of at least one analysis of the multiple analyses.

The pool maintenance system may include a controller; wherein the spectroscopic device may be configured to determine a signal to noise ratio of a result of an analysis executed by the spectroscopic device; and wherein the controller may be configured to determine at least one parameter of a future analysis based on the signal to noise ratio of the result.

The pool maintenance system may be a pool cleaning robot that may include a controller; wherein the spectroscopic device may be configured to determine a signal to noise ratio of a result of an analysis executed by the spectroscopic device; and wherein the controller may be configured to control a movement of the pool cleaning robot based on the signal to noise ration of the result and based on one or more scheduled analyses of the fluid of the pool by the spectroscopic device.

The spectroscopic device may be mechanically coupled to a shock absorber.

The pool maintenance system may include a cooling unit for cooling a sensor of the spectroscopic device using the fluid of the pool.

The pool maintenance system may include a housing; wherein the housing may include a thermal conductive region; wherein a sensor of the spectroscopic device is thermally coupled to the thermal conductive region.

The pool maintenance system may include multiple fluid conduits for receiving the fluid of the pool from multiple locations and a selection unit for selecting a selected conduit for providing the fluid to the spectroscopic device for a given analysis.

The pool cleaning robot may include a housing, a drive system, a brushing system, an electrical cable, battery system, a power supply, a pump, an impeller, inlet and outlet and a water filtering device.

The partly submerged motorized water surface skimmer may include motorized propulsion means, navigation system, solar panels, rechargeable batteries, inductive or wired battery recharging element, a debris collecting basket, bumpers or bumper wheels, electronic control box with or without wireless communications.

The free floating system may include a float and a ballasting mean and, solar panels, and a control unit, and a wireless communications pack.

The spectroscopic device may be removable from pool maintenance system.

There may be provided a method for analyzing a fluid of a pool, the method may include receiving one or more samples of a fluid of a pool; and analyzing the fluid of the pool, wherein the analyzing may include using a spectroscopic device associated with a pool maintenance system.

The pool maintenance system is selected of group consisting of a pool cleaning robot, a skimmer, a pool maintenance system that is coupled to a pool filtering system, a pool maintenance system that is included in a pool filtering system, a pool maintenance system that is mechanically coupled to the pool, a partly submerged motorized water surface skimming system and a pool maintenance free floating system that is at least partially submerged in the fluid of the pool when the pool is at least partially filled with the fluid of the pool.

The method may include performing an additional analysis of the fluid of the pool, the additional analysis is not a spectroscopic analysis.

The method may include self-cleaning the spectroscopic device.

The method may include preparing the pool maintenance system to a next analysis of the fluid of the pool.

The method may include sensing a status of a pool maintenance system, determining whether the status of the pool maintenance system facilitates an execution of a next analysis of the fluid of the pool; wherein when the status does not facilitate the execution of the next analysis then either changing the status of the pool maintenance system.

The method may include responding to a result of the analysis.

The responding to the result of the analysis may include scheduling a next analysis of the fluid of the pool.

The method may include scheduling multiple analyses of the fluid of the pool at different locations within the pool.

At least two locations of the different locations may be positioned at different distances from a bottom of the pool.

One location of the different locations may be at a bottom of the pool and another location of the different positioned may be at a waterline.

Two or more locations of the different locations may differ from each other by an orientation of the pool maintenance system when visiting the two or more locations.

The method may include receiving, by a controller of the pool maintenance system, a schedule of multiple analyses of the fluid of the pool and modifying the schedule based on at least one result of at least one analysis of the fluid of the pool.

The method may include determining, by the spectroscopic device, a signal to noise ratio of a result of an analysis executed by the spectroscopic device; and determining at least one parameter of a future analysis based on the signal to noise ratio of the result.

Any combination of any of the pool maintenance systems and/or any of the components of the pool maintenance systems and/or of any spectroscopic devices illustrated in the specification and/or the drawings may be provided.

Any combination of any method step illustrated in the specification and/or the drawings may be provided.

BRIEF DESCRIPTION OF THE DRAWINGS

In order to understand the invention and to see how it may be carried out in practice, a preferred embodiment will now be described, by way of non-limiting example only, with reference to the accompanying drawings.

DETAILED DESCRIPTION OF THE DRAWINGS

Figure 1:
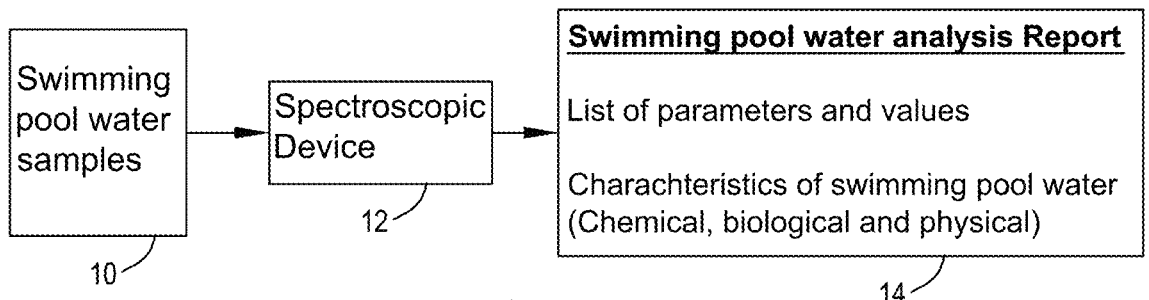
FIG. 1 is a schematic of a spectroscopic device and an analysis report according to an embodiment of the invention.

There is provided a system and method for performing spectroscopy of pool fluid that may use a micro total analysis system (MicroTAS) that is based on the employment of a 'micro' spectroscope or spectrometer to analyze and/or regulate pool fluid quality. A non-limiting example of a micro handheld size spectroscope (also referred to as a spectroscopic device) is the SCiO of consumer physics Inc.

The term pool means any vessel that is capable of containing fluid.

It can be established that the present invention relates to a miniaturized integrated spectroscopic sensor, with integrated sensed signal conditioning, signal exchange, and integration into a compact spectroscopic device for the measurement of solution and solvent-based chemistries. With adaptation, the spectroscopic device can be configured for solids or gases, but liquids are the preferred implementation. The sensed information is converted into meaningful information in the form of concentrations of specified species and for the composition or properties of mixtures and composite materials.

The present invention uses a miniaturized, low cost spectral sensing spectroscopic device, a major advancement in measurement opportunity over the current state of the art within the pool industry, and overcomes issues related to size or space occupied in the laboratory, or the size of a portable spectrometer. Each spectroscopic device is intended to provide the functionality of a normal spectrometer or spectral analyzer, but at reduced cost, and with a significantly reduced size for the total package.

Specifically, the invention relates to a spectroscopic device that may be included within, attached to or mechanically coupled to a pool maintenance system and/or to any part of the pool. The pool maintenance system may be a pool cleaning robot, a skimmer, a pool water filtering system, and the like.

A pool water filtering system may include, in very general terms, of an external closed loop system whereby fluid from the pool is pumped, by means of a pump, into a filtering spectroscopic device that returns the filtered fluid back to the pool.

The spectroscopic device may be configured to perform fluid analysis and transmission of said parameter results to a peripheral computing spectroscopic device whereby the computing spectroscopic device may further act to physically regulate the pool fluid treatment according to the analyzed results.

The importance of a spectrometer or spectroscopic device to pool preventive measures may be typically manifested when, for example, turbidity in the water is recognized (by means of a turbidity sensor, the spectroscopic device or even by visual inspection). The root cause of this is not easy to deduct or it may need further analysis. The analysis may deduct what is missing in the water chemistry that may be causing the imbalance in the levels of PH and/or alkalinity and/or chlorines and the like. The system and method in this patent specification is for a spectrometer that may analyze the levels of the chemicals and the residue of dead (or living) organic material (such as algae or bacteria) and thereby assist with analysis of a root cause of the turbidity or any other adverse water hygiene parameter by correlating analysis results. In some extreme cases, the spectroscopic device may communicate that the pool needs shock treatment (such as adding flocculants or clarifiers, amongst other). In less severe cases, it may for example, recommend preventing deterioration by adding specific doses of PH– (PH minus) or acid or other chemicals. In other cases, the water may be clear (not turbid) but the spectroscopic device will recognize a growing population of non-visible living organisms (algae, bacteria) that are still at an early stage of development. It may then recommend a specific dose of, for example, preventive chlorine to disinfect the pool water to halt further water hygiene deterioration. Recognizing such microorganisms in a pool early enough is difficult and more so to an average private home pool owner.

According to the preferred embodiment of the invention there may be provided at least one spectroscopic device (hereinafter: the spectroscopic device) for determining properties of a fluid in real-time, said spectroscopic device may include:

a. An integrated energy source and an integrated spectroscopic sensing detector package having a spectroscopic sensing detector.
b. A sample window or cell, disposed adjacent to said package, and dimensionally designed to match an active area of the spectroscopic sensing detector.
c. Integrated electronics coupled to said package for providing energy for said source and for receiving a signal generated by said spectroscopic sensor in response to energy coupled to said detector by said sample window or cell, said integrated electronics providing direct output of sample properties of said sample;
d. Said integrated electronics having on-board computer processing with a microcomputer or digital signal processor, and;
e. Said integrated electronics having on-board data communications including output to at least one of a visual display, communications of results to a process monitoring computer, and an option for wireless communications to a network.
f. Using analysis results to activate a regulating fluid treatment system either automatically or on command of a user.
g. The spectroscopic sensing spectroscopic device may act without contact or sampling of the fluid.
h. A software controlled timer and actuator to initiate start and end of testing analysis and communications thereof to end users.
i. A software controlled mechanical shifting of wavelengths and/or lens angles.

The spectroscopic device may be based on Raman, ultraviolet (UV)/Vis (visual light), Fluorescence, infrared (IR)/Near-IR spectroscopy or any other spectroscopic sensing methodology.

The said on-board computer processing may include a memory for data, calibration coefficients, methods and results.

The communication of results to a process monitoring computer control or automation system is used to command operations of a variety of spectroscopic devices to better process and treat the fluid under analysis.

The results may include data on levels of Chlorine, Total Dissolved Salts (TDS), Turbidity, Phosphates, Temperature, pH, ORP, Flow Rate, Algae, Bacteria, circulated fluid flow rates in the filtering system, and any or all other physical, chemical and biological parameters or species.

The communication of results may be interpreted for the goal of stabilizing and maintaining pool fluid quality and be sent to an automated regulation system of fluid that dispenses chemical compounds into the pool maintenance system.

The sample window or cell allows for continuous monitoring of a continuous stream of fluid circulating in a pool.

The sample window or cell surface allows for self-cleaning.

The self-cleaning is done by means of acoustic vibrations, mechanical swiping, etc. that may be connected and activated by the spectroscopic device.

The spectroscopic device may comprise of a kit that includes a pipe saddle and fittings to attach the spectroscopic device to a pool filtering system piping.

In another embodiment, the spectroscopic device may be installed or connected to pool equipment.

The spectroscopic device may be installed or connected to pool equipment that is an automatic pool cleaning apparatus.

The spectroscopic device of this first embodiment may be a fluid proof spectroscopic device that may be battery operated using replaceable rechargeable batteries.

The said pool apparatus has the ability to receive data being wirelessly transmitted from the spectrometer that is located inside its hollow body.

The transmission may be performed wirelessly underwater by means of a Bluetooth® electronic card that will emit data to a PCB or CPU control unit inside the pool cleaner control box or a central motor unit.

The data may be further sent by means of the pool cleaner electrical cable to an external unit such as the pool cleaner's power supply.

The power supply may be able to emit the data—by means of Bluetooth® or a Wi-Fi from the spectroscopic device—to any receiving communication utility: a home computer, smartphone and the like.

The spectroscopic device of this first embodiment may also be wired to the said PCB or CPU control unit inside the pool cleaner control box or a central motor unit.

In yet another, second embodiment, the spectroscopic device may be installed or connected to pool equipment that is a skimmer inlet.

The spectroscopic device of this second embodiment may be a waterproof spectroscopic device that may also battery operated using replaceable batteries.

The spectroscopic device of this second embodiment will be connected or attached to the inside area of the skimmer so that the light beam be directed at the fluid to register fluid quality parameters.

The spectroscopic device of this second embodiment will be connected or attached to the inside area of the skimmer may be able to wirelessly communicate by means of Bluetooth® or Wi-Fi to any receiving communication utility such as a smartphone.

All communications of both first and second embodiments are intended to advise the end user about the state of the pool fluid.

All communications of the preferred embodiment are meant to advise the end user about the state of the pool fluid and automatically—or subject to a manual command—proceed to activate the dosing equipment to regulate the chemistry composition of the pool fluid.

The spectroscopic devices of both the first and second embodiments may be removable.

The spectroscopic devices of both the first and second embodiments may be used as hand held spectroscopic devices.

It is a main feature across this specification to employ miniaturized, hand held spectroscopic devices or spectrometers.

The term 'spectroscopy' or 'spectroscopic' or 'spectrophotometry' means any process of analyzing the interaction between radiated energy and matter. The term spectrometer means a device which provides qualitative and quantitative identification of materials based on spectroscopic analysis.

FIG. 1 is a schematic of a spectroscopic device 12 and an analysis report according to an embodiment of the invention.

The spectroscopic device 12 receives samples of pool fluid 10, analyzes the fluid and outputs a pool analysis report 14.

According to an embodiment of the invention the spectroscopic device may be configured to analyze a fluid of a pool.

According to an embodiment of the invention the spectroscopic device may be configured to apply any number of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy (h) reflectance ultra-violet-visible spectroscopy.

According to an embodiment of the invention an applying of one or more spectroscopic techniques (such as the spectroscopic techniques mentioned above) may include applying a chemometric algorithm.

Chemometric is applied to solve both descriptive and predictive problems in experimental natural sciences, especially in chemistry. In descriptive applications, properties of chemical systems are modeled with the intent of learning the underlying relationships and structure of the system (i.e., model understanding and identification). In predictive applications, properties of chemical systems are modeled with the intent of predicting new properties or behavior of interest. In both cases, the datasets can be small but are often very large and highly complex, involving hundreds to thousands of variables, and hundreds to thousands of cases or observations.

Chemometric techniques (see: www.wikipedia.org) are particularly heavily used in analytical chemistry and metabolomics, and the development of improved chemometric methods of analysis also continues to advance the state of the art in analytical instrumentation and methodology. It is an application driven discipline, and thus while the standard chemometric methodologies are very widely used industrially, academic groups are dedicated to the continued development of chemometric theory, method and application development.

Chemometric may include applying one or more multivariate calibration techniques, supervised multivariate classification techniques, unsupervised classification techniques, multivariate curve resolution, multivariate statistical process control (MSPC), and multiway methods.

The inventors found that applying a chemometric algorithm may improve the analysis of the fluid. For example—when using NIR spectroscopy the chemometric algorithm can significantly improve the analysis.

The inventors found that a single spectrometric method may provide some useful information, but more than one method may have to be applied.

The inventors found that that Ultra-Violet absorption spectroscopy and Ultra-Violet fluorescence spectroscopy are good candidates for monitoring pool fluid.

The inventors found that SERS (surface enhanced Raman spectroscopy) is another good candidate for monitoring pool fluid.

The inventors found that IR spectroscopy with a comparison to a reference may be a good candidate for monitoring pool fluid.

The inventors found that spectroscopic data may provide more detailed information than non-spectroscopic fluid analysis methods. For example, information of some organic contaminants and on biological species might be extracted from fluorescence data obtained by fluorescence spectroscopy. Non-limiting examples may include specific, real time digital data about urine or turbidity levels in a pool that are practically impossible to automatically asses with present day equipment.

The inventors found that having one or more additional sensors (that are not spectroscopy based sensor) may further improve the quality of the fluid analysis.

According to an embodiment of the invention an applying of one or more spectroscopic technique may include analyzing one or more of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

A sub-region of a wavelength range may include one or more wavelengths. A sub-region may include a continuous sequence of wavelengths within a wavelength range, a non-continuous combination of frequencies within the wavelength range or a combination thereof.

According to an embodiment of the invention an applying of one or more spectroscopic technique may include analyzing one or more wavelengths ranges and/or one or wavelength sub-regions that substantially equal the mentioned above wavelengths ranges and/or one or wavelength sub-regions. The term "substantially" means that a pre-defined deviation is allowed. The predefined deviation may be, for example, up to thirty nanometers, up to twenty percent, and the like.

For example, referring to the wavelength range between one hundred eighty nanometers and two hundred nanometers—a wavelength range that substantially equals said wavelength range may (a) range between one hundred fifty nanometers till two hundred and thirty nanometers, or (b) range between one hundred eighty nanometers till two hundred and thirty nanometers, or (c) range between one hundred fifty nanometers till two hundred nanometers, and the like.

According to an embodiment of the invention the spectroscopic device may analyze one or few wavelength ranges or sub-ranges—instead of scanning a large wavelength range- and this dramatically reduces the cost of the spectroscopic device. This also allows using optical components (such as filters, lenses and lasers) that are fitted to a relatively narrowband and thus are cheaper than broadband compliant optical components.

Alternatively—the illumination and/or collection can involve broadband illumination and/or collection.

According to an embodiment of the invention an applying of one or more spectroscopic technique may include applying the one or more spectroscopic technique at a resolution of one nanometer, at a resolution that does not exceed one nanometer or at a resolution that exceeds one nanometer (nm).

Non-limiting examples of resolution may include 0.1 nm, 0.2 nm, 0.3 nm, 0.4 nm, 0.5 nm, 2 nm, 3 nm, 4 nm, 5 nm, 6 nm, 7 nm, 8 nm, 9 nm, 10 nm, and the like. Etc.).

According to an embodiment of the invention the system may include one or more additional sensors—an additional sensor is assumed to differ from a spectroscopic sensor.

According to an embodiment of the invention the at least one additional device may include at least one (or any combination of) the following sensors: (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

According to an embodiment of the invention the system may include a self-cleaning mechanism for cleaning a spectroscopic sensor of the spectroscopic device.

When the system includes one or more additional sensors, that system may also include self-cleaning mechanism for cleaning the one or more additional sensors (that are not a spectroscopic sensor).

The cleaning mechanism may be at least one out of (a) and acoustic vibrator, (b) a mechanical cleaning element that may be configured to clean an optical element of a sensor of the system (such as a lens), the mechanical cleaning element may be, for example, (a) a brush, (b) a rag, (c) a wiper, and (d) a Teflon sphere.

According to an embodiment of the spectroscopic device, it may include a pool filtering system pipe or conduit, optics that are configured to direct electromagnetic radiation through an opening formed in the pipe and to receive electromagnetic radiation from the fluid.

According to an embodiment of the invention the optics are positioned within a saddle that interfaces and is secured to the said pipe.

The said spectroscopic device and its saddle may be part of a kit that may be installed by an end user onto the said pipe or conduit.

According to an embodiment of the invention the spectroscopic device is calibration free.

According to an embodiment of the invention the spectroscopic device is reagent free.

The spectroscopic device may make advantage of the water environment to include a water-cooling system instead of a dedicated cooling device in order to cool down to sensors and the device.

The system may be a pool cleaning robot that may include a housing, drive system including wheels and/or tracks, electrical cable or on-board batteries, an electronic control box, pump and impeller, inlet and outlet and a water filtering device.

The spectroscopic device may include at least one out of (a) a spectroscopic sensor that extends outside a housing of the pool cleaning robot such as the front, (b) an interface for coupling a battery operated spectroscopic device to the pool cleaner, (c) a spectroscopic sensor that is positioned within a housing of the pool cleaning robot, (d) a spectroscopic sensor that is positioned at a bottom portion of the pool cleaning robot, (e) the spectroscopic sensor may be electrically coupled to (and/or incorporated within) a motor unit, (f) a spectroscopic sensor that is positioned at a rear portion of the pool cleaning robot, (g) a spectroscopic sensor that is positioned at a left portion of the pool cleaning robot.

The spectroscopic device included in or attached to the pool maintenance system may be classified waterproof such as models produced by Spectronic Devices Ltd., Bedfordshire, United Kingdom that may also be battery operated using replaceable batteries.

The spectroscopic device that may be removably or permanently attached to the pool maintenance system may be configured to be attached to a chassis comprising shock absorbers mounted on a damping device mounted on the chassis. This may be of particular importance to the pool cleaner in order to avoid spectronomy pixel resolution and accuracy distortions when it bounces against underwater obstacles such as walls.

According to an embodiment of the invention the spectroscopic device may be configured to provide comprehensive analysis information (chemically, biologically and physically) accurately, reliably and continuously. The spectroscopic device may perform the spectroscopic analysis without using reagents, in a robust manner, without any calibration, be inexpensive, and according to the comprehensive measurement and analysis enables reaching of intelligent conclusions and as a result enables effective treatment or other remedies to the pool fluid.

The spectroscopic device may provide a comprehensive pool fluid analysis that may include a chemical analysis (chemical compound such as: free Chlorine, combine Chlorine, Calcium, Cyanuric-acid, etc.), a biological analysis (organic materials such as: sweat, urine, plants, microorganisms, etc.) and a physical analysis (temperature, pressure, turbidity, etc.).

This analysis may improve any fluid treatment process by reducing chemicals consumption, reduce fluid consumption, reduce energy consumption, reduce a number of particles in fluid, reduce skin and/or eye irritation, reduce fluid hazards, and extend the lifespan of the pool filtering system.

Figure 2:
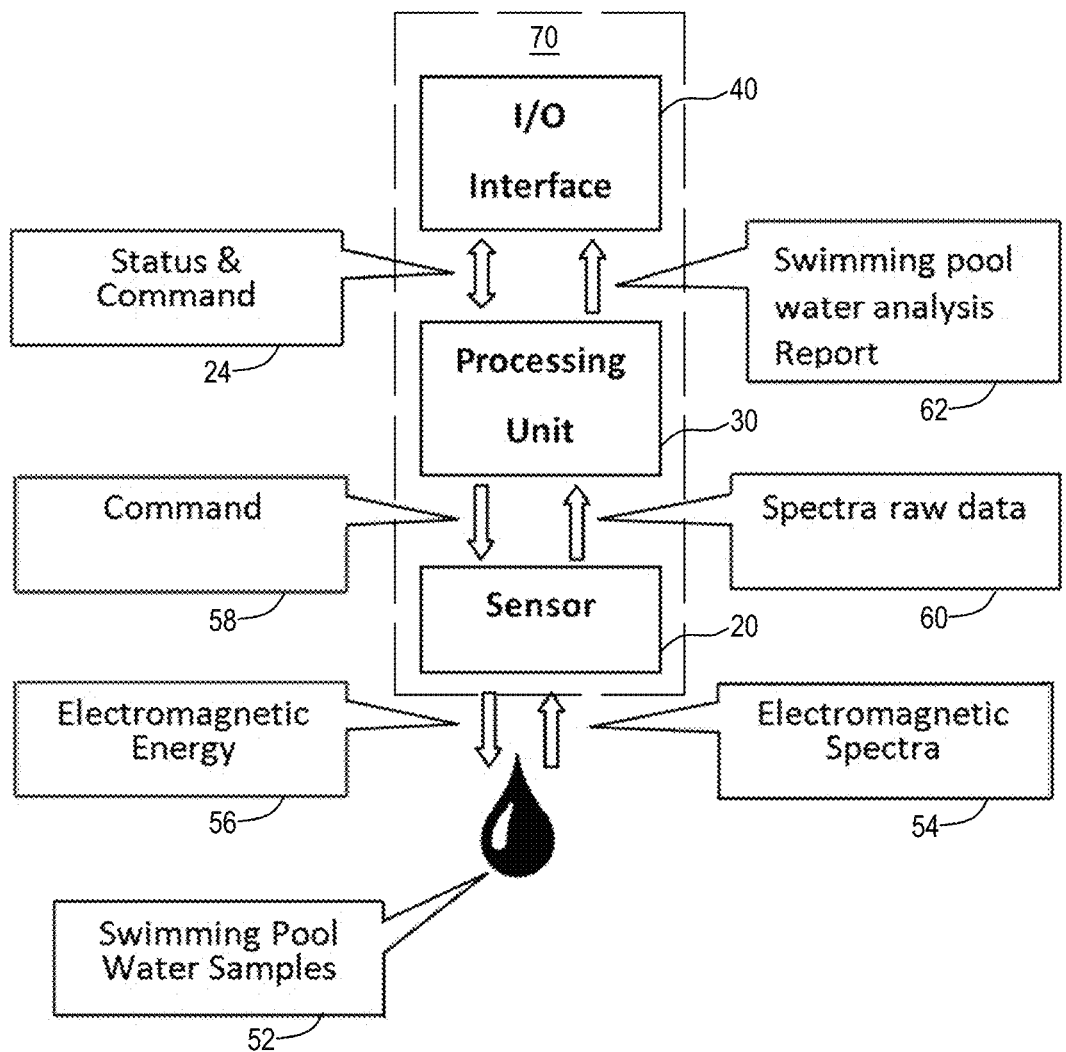
FIG. 2 illustrates an analysis process according to an embodiment of the invention.

FIG. 2 illustrates an analysis process according to an embodiment of the invention.

The spectroscopic device 70 includes sensor 20, processing unit 30 and input output (IO) interface 40.

The sensor 20 may include optics for directing electromagnetic radiation 56 towards a pool fluid sample 52 and for receiving electromagnetic spectra 54 from the pool fluid samples—resulting from the illumination of the pool fluid samples 52 by electromagnetic radiation 56. The electromagnetic spectra 54 can result from absorbance and/or fluorescence.

The sensor 20 generates spectra raw data (such as intensity or power per wavelength) 60 that is sent to processing unit 30. Processing unit 30 processes the spectra raw data (for example by applying a chemometric algorithm) to provide the pool analysis report 14 to the IO interface 40.

The pool analysis report 14 may be any arrangement of information that represents one or more quality, parameters or characteristics of the fluid.

IO interface 40 may transmit (wirelessly or non-wirelessly) the pool analysis report 14 to another device, may display the pool analysis report 14 to a user, be connected to an alarm or another warning device and the like. IO interface 40 may send status and command 24 to the processing unit 30 that may send commands to the sensor 20.

The spectra raw data can be processed (by processing unit 30) by applying a chemometric algorithm and translated into a list of parameter values that represent the compounds present in the fluid.

The spectra raw data can be used to determine kinetics of fluid chemistry and make predictions of fluid quality and treatment required not otherwise possible. Frequency of spectra and kinetic determinations can be generated over minutes, hours, days or weeks (see below).

In FIGS. 3-10 any reference to a spectroscopic device may be regarded as a reference to a sensor of the spectroscopic device. Other components of the spectroscopic device can be located elsewhere—and receive spectra raw data from the sensor via a communication link.

Figure 3:
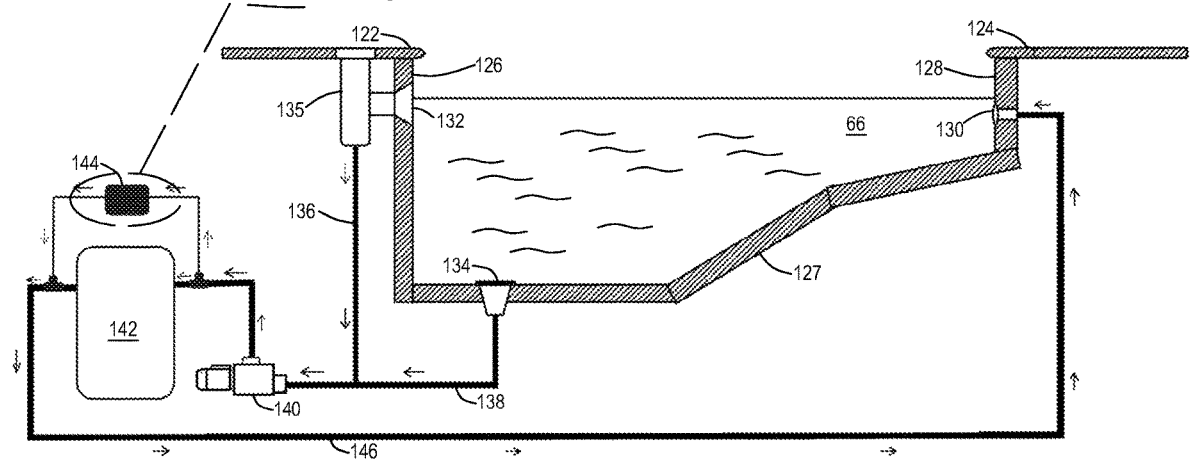
FIG. 3 illustrates a spectroscopic device that is embedded in a pool filtering system according to an embodiment of the invention.

FIG. 3 illustrates spectroscopic device 144 that is a part of a pool filtering system according to an embodiment of the invention.

The pool filtering system is configured to filter the fluid of a pool that includes bottom 127, right sidewall 128, left sidewall 126 and contains fluid 66. Fluid is sucked through skimmer opening 132 (formed in left sidewall 126) of skimmer 135 and through drain 134 (formed in bottom 127) propagates through pipes 136 and 138 towards pump 140 and is then sent to filter 142 and (in parallel) to spectroscopic device 144.

Thus, spectroscopic device 144 may analyze fluid that passes through the pool filtering system. The filtered fluid and the analyzed fluid are fed back through pipes 146 to an outlet or jet 130 formed in right sidewall 128. FIG. 3 also illustrates the upper surface/edge or pool deck 122 and 124 that surrounds the pool.

It is noted that the spectroscopic device 144 may positioned in various other locations—for example it may be positioned within skimmer 135, in proximity to drain 134, may sample fluid flowing through each one of pipes 136 and 138, may precede pump 140, may sample fluid between pump 140 and filter 142, or at the input of 132 and the like.

It is further noted that the fluid filtering system may differ from the fluid filtering system of FIG. 3. For example, the fluid filtering system may receive fluid via only one of skimmer 135 and drain 138, may not include a skimmer, may include more than two openings for receiving pool fluid, may be positioned above the pool, and the like.

Figure 4:
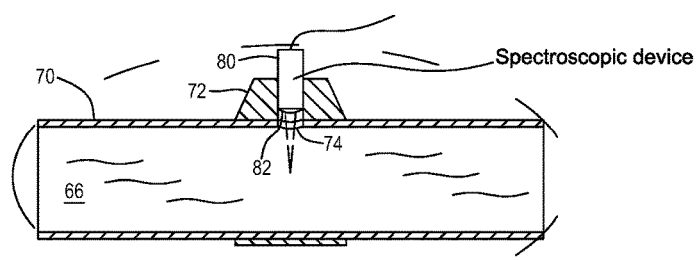
FIG. 4 is a cross section of a pipe and a spectroscopic device that is configured to analyze the fluid that flows through the pipe according to an embodiment of the invention.

FIG. 4 is a cross section of a pipe 70 and a spectroscopic device 80 that is configured to analyze the fluid that flows through the pipe according to an embodiment of the invention.

Fluid 66 that flows through pipe 70 is illuminated by electromagnetic spectra that propagate through opening 74 within pipe 70. In FIG. 4 the electromagnetic spectra 54 from fluid 66 passes through the opening 74 although the electromagnetic spectra may pass through another opening (not shown). FIG. 4 illustrates a lens 82 of the spectroscopic device 80. It is noted that the spectroscopic device 80 may include additional optical components.

Opening 74 may be a transparent or partially transparent window or cover.

Spectroscopic device 80 of FIG. 4 may include a processing unit and/or an IO interface (see FIG. 2)—although the processing device and/or the IO interface may be positioned elsewhere.

In FIG. 4 the spectroscopic device 80 is connected to pipe 70 via a saddle 72. It is noted that spectroscopic device 80 may be positioned within pipe 70 or attached to the pipe 70 is any other manner.

Figure 5:
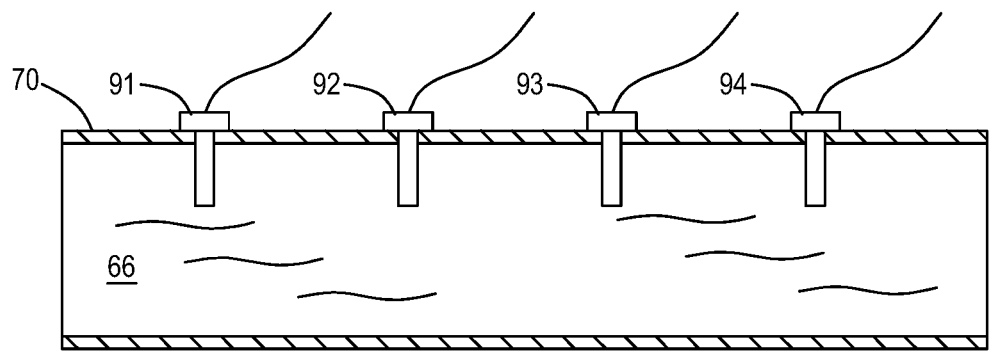
FIG. 5 is a cross section of a pipe and multiple additional sensors that are configured to sense various elements within the fluid that flows through the pipe according to an embodiment of the invention.

FIG. 5 is a cross section of a pipe 70 and multiple additional sensors 91, 92, 93 and 94 that are configured to sense various elements within the fluid that flows through the pipe according to an embodiment of the invention.

There may be one, two, three, four or more than four additional sensors. The one or more additional sensors may be positioned close (within few centimeters) from spectroscopic device 80 or may be spaced apart from spectroscopic device 80.

The one or more additional sensor may be selected out of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric acid sensor, (l) an Alkalinity sensor, (m) a Salinity sensor.

Figure 6:
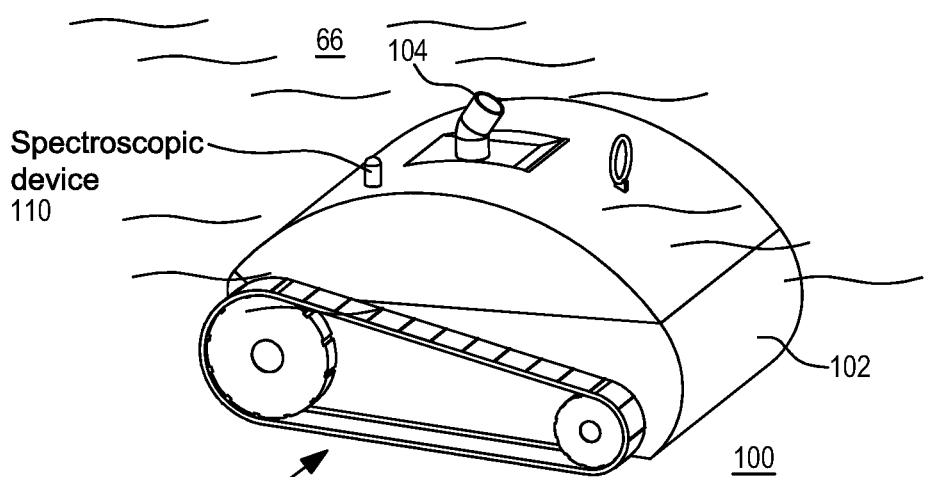
FIG. 6 illustrates a pool cleaning robot that comprises a spectroscopic device according to an embodiment of the invention.

FIG. 6 illustrates a pool cleaning robot 100 that includes a spectroscopic device according to an embodiment of the invention.

FIG. 6 illustrates that the sensor 110 of the spectroscopic device extends outside housing 102 of the pool cleaning robot 100.

Sensor 110 may be positioned at any position in relation to the housing 102—at the upper portion, at the lower portion, at a right part of housing 102, at the left portion of housing 102 and the like.

The sensor 110 may be positioned within housing and preferably before a filtering unit (not shown) of the pool cleaning robot 100.

The pool cleaning robot 100 may include a propulsion system that may include a motor, gear and interfacing elements such as tracks and rotating wheels (collectively denoted 106 in FIG. 6), wheels of a trackless pool cleaning robot, and the like. The pool cleaning robot also includes a filtering unit that may receive fluid through an inlet and output filtered fluid through an outlet (such as outlet 104 of FIG. 6).

The pool cleaning robot 100 may perform the spectroscopic analysis while being static, during movement, during filtering periods in which the pool cleaning robot filters the fluid of the pool, outside a filtering period, in a partially overlapping manner with the filtering process, and the like.

The pool cleaning robot 100 may perform multiple spectroscopic analysis iterations and assign time stamps/location information to the different spectroscopic analysis iterations. This may enable to map the outcome of the different spectroscopic analysis iterations to different locations within the pool and/or to different times.

For example, the pool cleaning robot 100 may compare results of spectroscopic analysis iteration before a filtering process to results of a spectroscopic analysis iteration conducted after a filtering process to evaluate the filtering process.

Another example may include the pool cleaner sampling pool water at or near the waterline during wall climbing. Because chlorine concentrations are enforced statutorily in many countries especially for public pools, it may be of importance to assess the differences of chlorine concentration levels between the bottom of the pool (near the floor) to that at the waterline due to chlorine sunlight UV degradation the closer one gets to the waterline. This may, for example, reduce or eliminate the commonly highly corrosive cyanuric acid supplements used to protect chlorine concentrations.

Yet for another example—the pool cleaning robot may be configured to provide a map of spectroscopic analysis iteration results and locations within the pool, during different times of the days or periods or seasons of the year or when the pool is being very crowded or less crowded, thereby allowing a pool owner to detect problems related to different regions of the pool.

Figure 7:
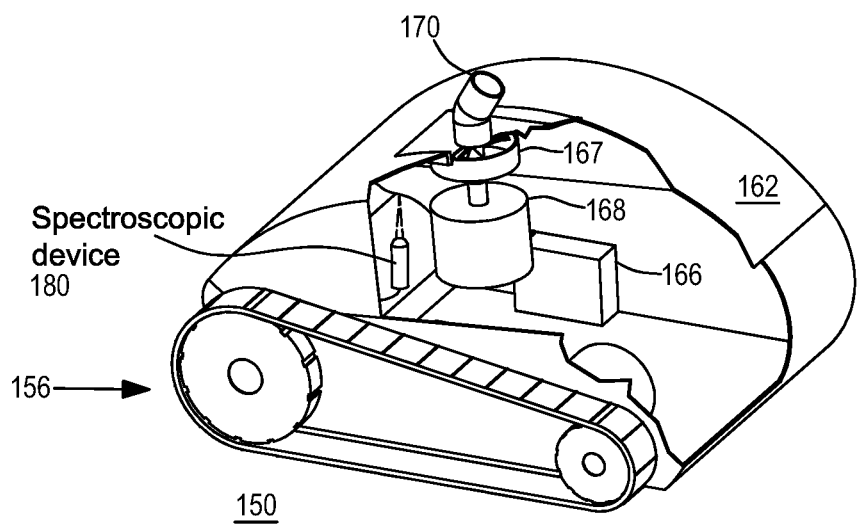
FIG. 7 illustrates a pool cleaning robot that comprises a spectroscopic device according to an embodiment of the invention.

FIG. 7 illustrates that the sensor 180 of the waterproofed spectroscopic device is included within housing 162 of pool cleaning robot 150, according to an embodiment of the invention.

In FIG. 7 the pool cleaning robot 150 is illustrated as including propulsion unit 156, impeller 167, pump motor 168 for rotating the impeller, and controller 166. FIG. 7 also shows turbine 163 and turbine motor 164.

In another embodiment, controller 166 may also comprise the spectroscopic device 180. In yet another common embodiment, a motor unit (not shown) may comprise the controller 166, at least one pump 168, at least one drive motor and the spectroscopic device that are all located within a water sealed box.

Figure 8:
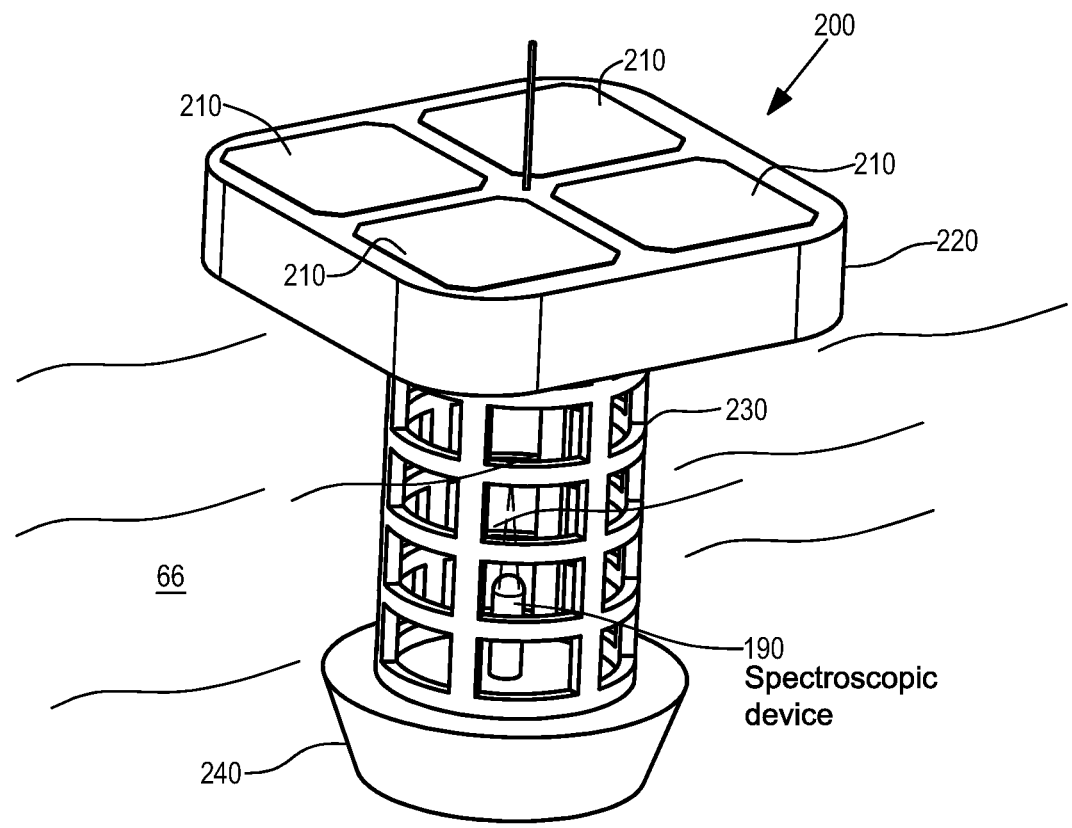
FIG. 8 illustrates a system that includes a floating unit, a submerged unit and a spectroscopic device according to an embodiment of the invention.

FIG. 8 illustrates a system 200 that includes a floating unit 220, a submerged unit and a spectroscopic device 190 according to an embodiment of the invention.

System 200 includes a submerged unit that includes grid 230 and a bottom 240. The grid 230 and the bottom 240 are submerged when the system 200 is placed in a pool. The spectroscopic device 190 may analyze fluid that flow through the apertures of grid 230.

The floating unit 220 may include photovoltaic cells 210 (arranged in one or more panels) for supplying power to system 200. Additionally or alternatively, system 200 may include a battery or any other power supply and a control PCB.

It is further noted that part of the grid 230 may be above the fluid level and include a PCB communications antenna.

System 200 may float freely in the pool (a free floating system). It may or may not be attached to the pool or to any other structural element and may contain an onboard chemical compound dispenser facility such as a flocculant (not shown).

System 200 may further include floats and ballasting weights to keep the system floating normal at and in relation to the water surface. Solar panels to power on board control and wireless communications pack. The submerged, removable, waterproof, battery operated spectroscopic device 190 may be attached to the grid 230 with a communication antenna being able to wirelessly communicate via or through the floating unit 220.

Figure 9:
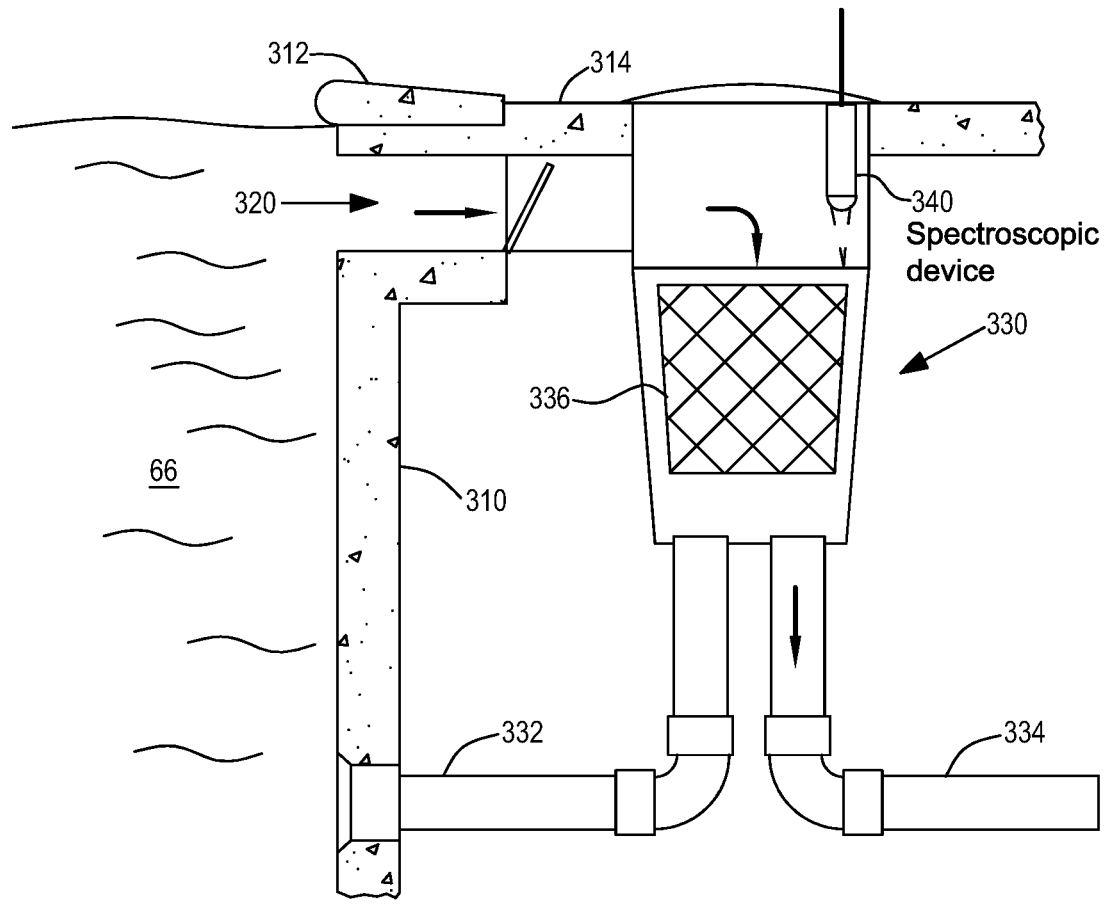
FIG. 9 illustrates a skimmer that includes a spectroscopic device according to an embodiment of the invention.

FIG. 9 illustrates a skimmer 330 and a spectroscopic device 340 according to an embodiment of the invention.

Skimmer 330 includes a skimmer opening 320 for receiving fluid from the pool, filter basket 336, first outlet pipe 332 for supplying fluid that passed through filter basket 336 to the pool and second pipe 334 for providing pumped fluid to other parts of a pool filtering system such as a main filter. The submerged, removable, waterproof, battery operated spectroscopic device 340 may be attached to the basket with a communication antenna being able to wirelessly communicate via or through the skimmer manhole cover in the deck 314.

The skimmer opening is formed in a sidewall 310 of the pool near an edge 312 and upper surface or pool deck 314 surrounding the pool.

Figure 10:
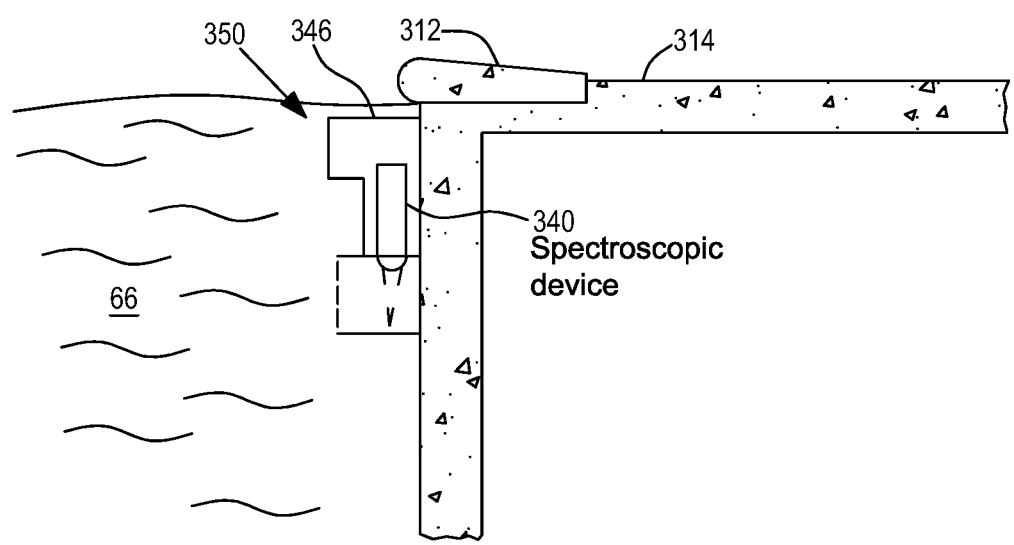
FIG. 10 illustrates a system that is attached to a sidewall of a pool and includes a spectroscopic device according to an embodiment of the invention.
Figure 11:
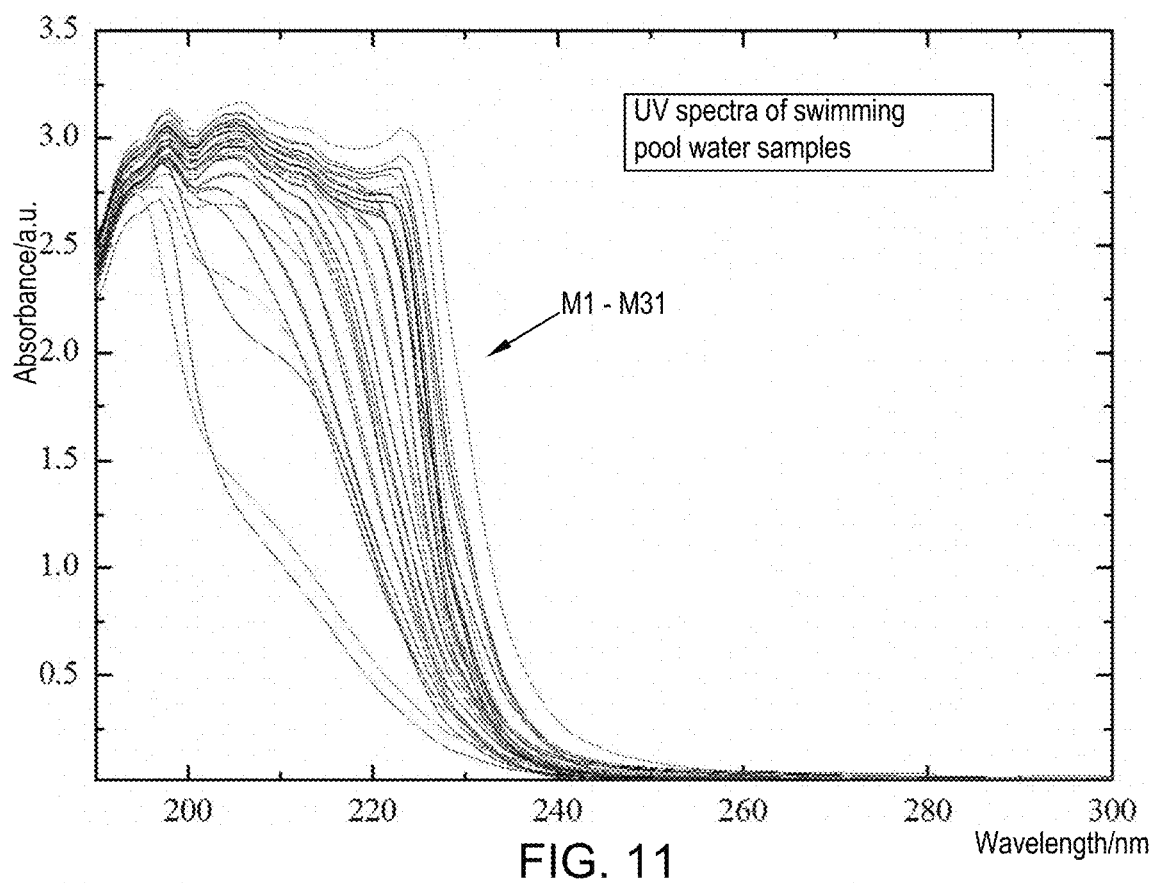
FIGS. 11-15 illustrate fluid samples spectroscopic fingerprints according to an embodiment of the invention.
Figure 12:
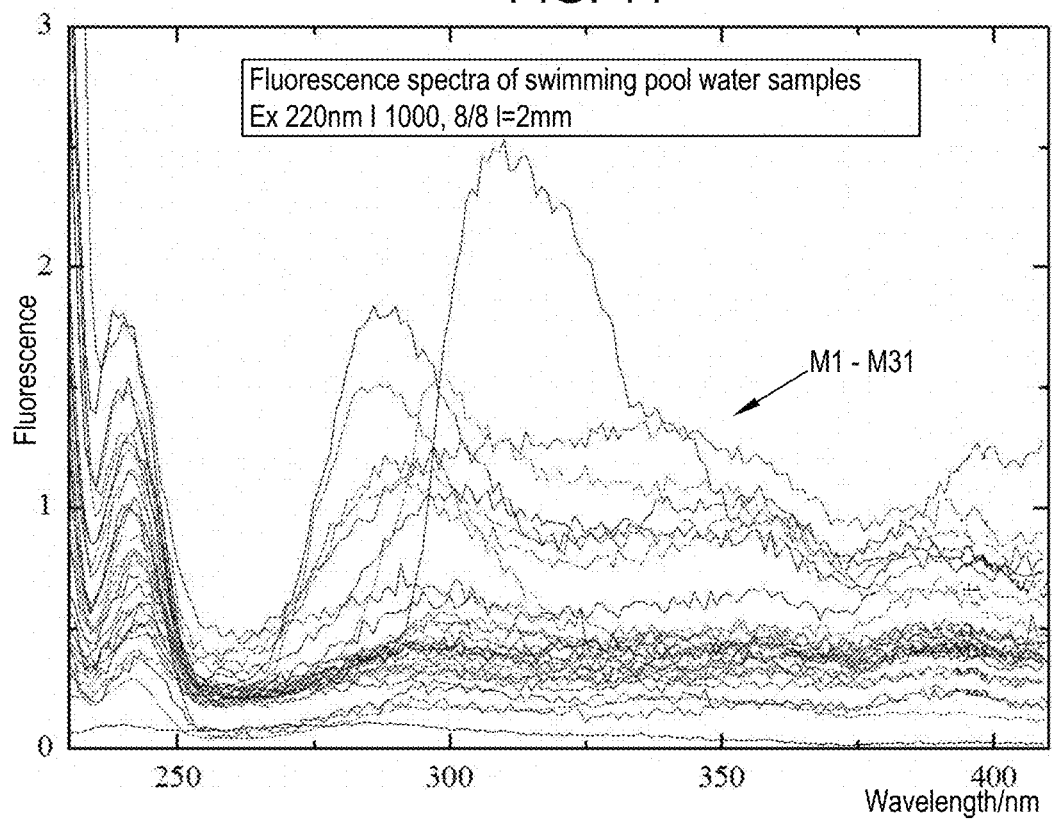
Figure 13:
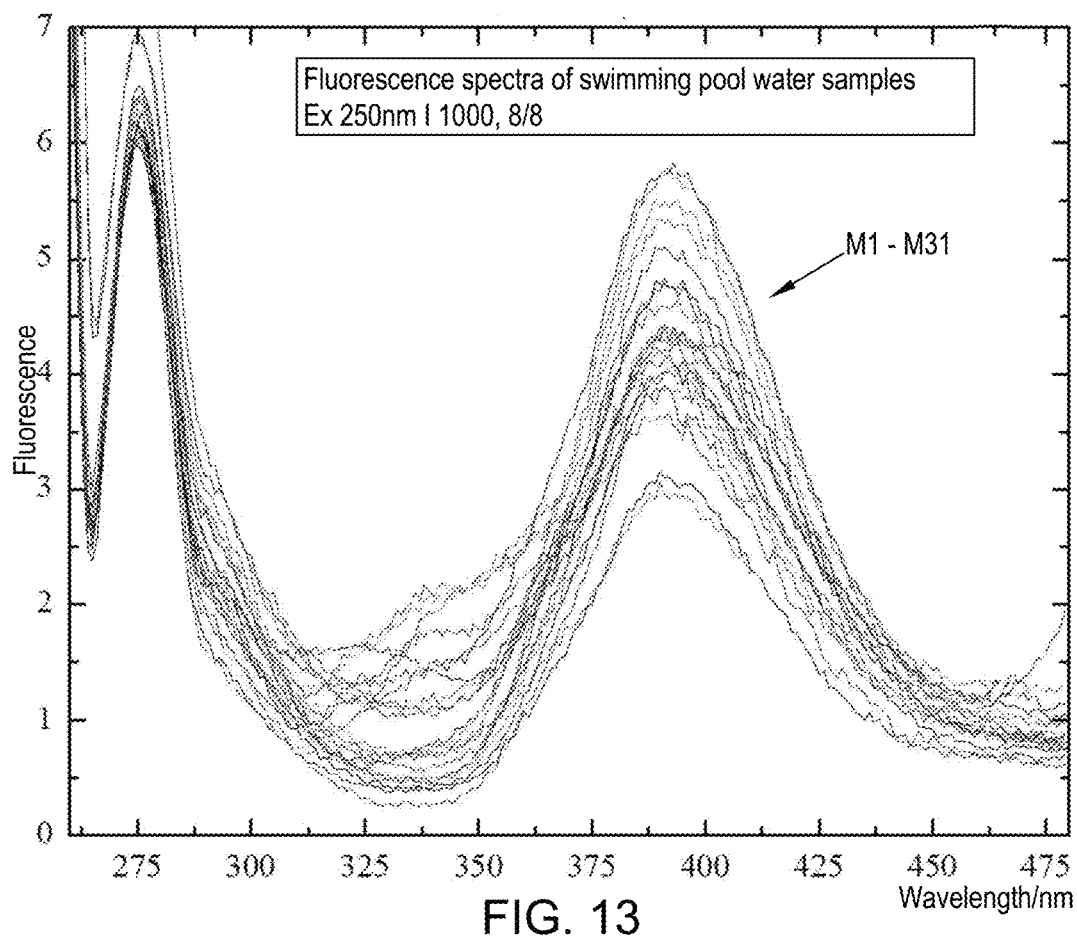
Figure 14:
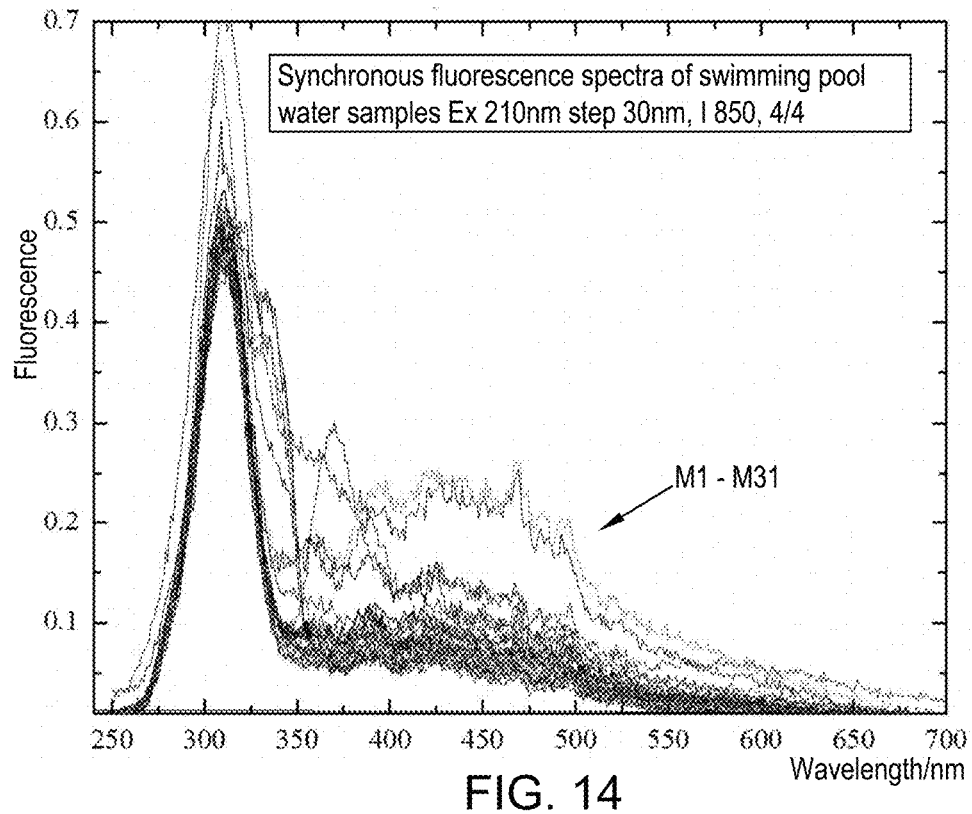
Figure 15:
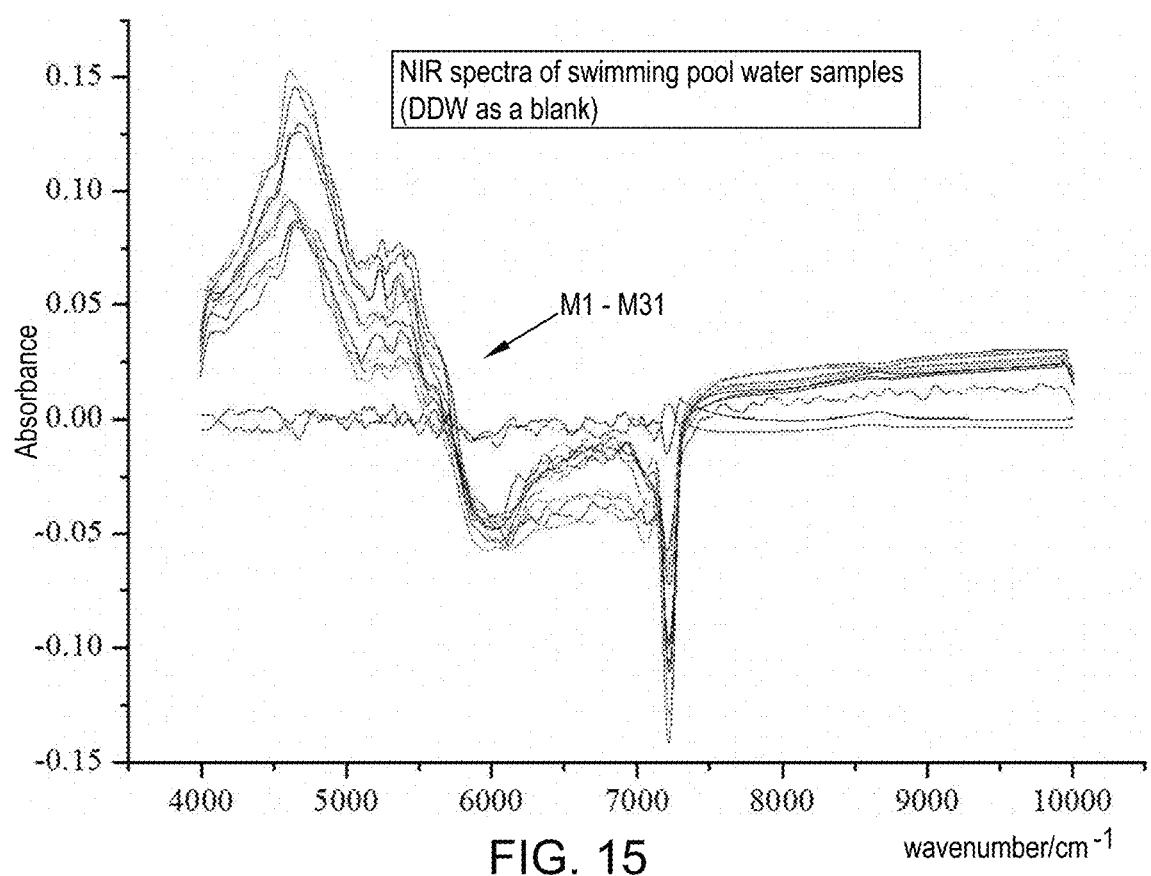

FIG. 10 illustrates a system 350 that is attached (by interface 346) to a sidewall of a pool and includes a submerged, removable, waterproof, battery operated spectroscopic device 340 with a communication antenna from the PCB (not shown) according to an embodiment of the invention.

Interface 346 may detachably or non-detachably connect the submerged, removable, waterproof, battery operated spectroscopic device 340, that is located within the interface, to the sidewall of the pool (by means of, for example, suction cups) and contain a PCB and a PCB communication antenna (not shown).

According to an embodiment of the invention the spectroscopic device (with or without one or more additional sensor) may be configured to calculate at least one of the following fluid quality parameters: (a) Free available chlorine: Hypochlorous acid (HOCl) plus hypochlorite ion (OCl—) for example— within a relevant concentration range of 0.1-10 parts per million (ppm), (b) combined available chlorine: Chloramines or compounds formed when free chlorine reacts with organic nitrogen-containing compounds. (NH2Cl, NHCl2, NCl3), (c) Total Chlorine: free available chlorine plus combined available chlorine. For example—the relevant concentration range may be 0.1-3 ppm, (d) Cyanuric Acid. For example—the relevant concentration range may be 10-150 ppm, (e) Salinity: total dissolved salts. For example—the relevant concentration range may be up to 5000 ppm, (f) Alkalinity: Bicarbonate. For example—the relevant concentration range may be 20-500 ppm, (g) pH, (h) Turbidity, (i) common contaminants.

Non-limiting examples of common contaminants that can be detected by the system may include: (a) contamination from pool users, including bodily excretions, lotions, sunscreens, cosmetics, etc. These materials include parabens, N, N-diethyl-meta-tolu amide (DEET), caffeine and tris(2-carboxyethyl)phosphine (TCEP), (b) contamination from the source fluid used, including humic acids, chlorophyll a, metabolites of aqueous organisms, aliphatic hydroxy acids, aromatic carboxylic acids and some inorganic compounds as bromates, (c) contamination from reactions between disinfectants and the organic components, known as disinfection byproducts (DBPs). There are over 700 DBPs that have been identified in disinfected fluids e.g. trihalomethanes, haloacetic acids, etc., (d) Viruses, bacteria and protozoa in pool fluid are of considerable concern. Viruses relevant to pools include: Adenovirus, Hepatitis A virus (HAV), Echovirus and Norwalk virus. Bacteria which have been linked to pool related disease include: *Mycobacterium marinum, Mycobacterium avium, Pseudomonas aeruginosa, Escherichia coli, Legionella* spp. and *Leptospira interrogans*. Protozoa relevant to pools include *Cryptosporidium parvum, Giardia lamblia, Naegleria* spp. and *Acanthamoeba* spp., (e) Suspended particulates. The suspended particulates include inorganic particulates, organic particulates and particulates of biological nature. The size distribution might be very wide, starting with nanoparticles and up to microparticles. Currently, the particulates in pools are characterized by the turbidity, which definitely not a sufficient parameter.

FIGS. 11-15 illustrate unique pool fluid sample fingerprints using each spectroscopic method. Each pool has a unique physico-chemo-biological fingerprint; this fingerprint can be determined via optical spectroscopy according to the invention described herein. The spectroscopic results from this set of pools imply that the spectral data can be used as a fingerprinting tool. Almost all samples had significant changes in their UV absorption and fluorescence spectra. This might imply that a chemometric analysis of the spectra can characterize the individual condition of the pools. Nevertheless, it is well known that the performance and reliability of multivariate analysis algorithms is the best when the training set (the set of data used for finding the hidden correlations) is large.

Figure 16A:
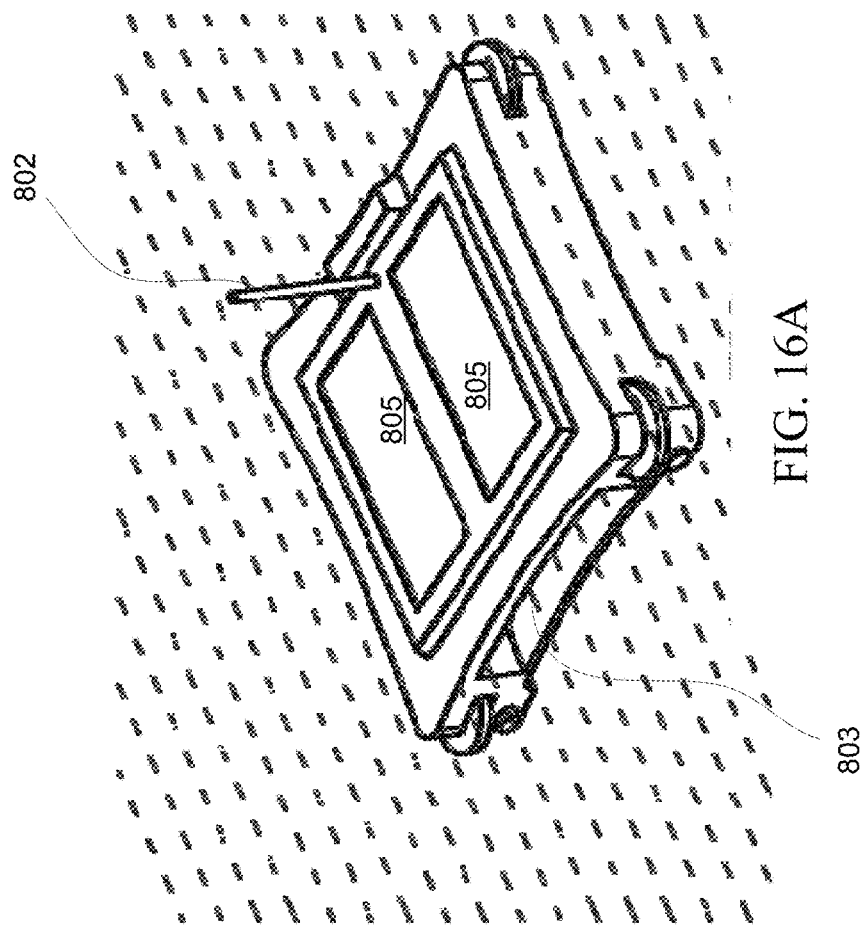
FIGS. 16A and 16B illustrates a waterline leaves and debris motorized skimming pool cleaning robot.
Figure 16B:
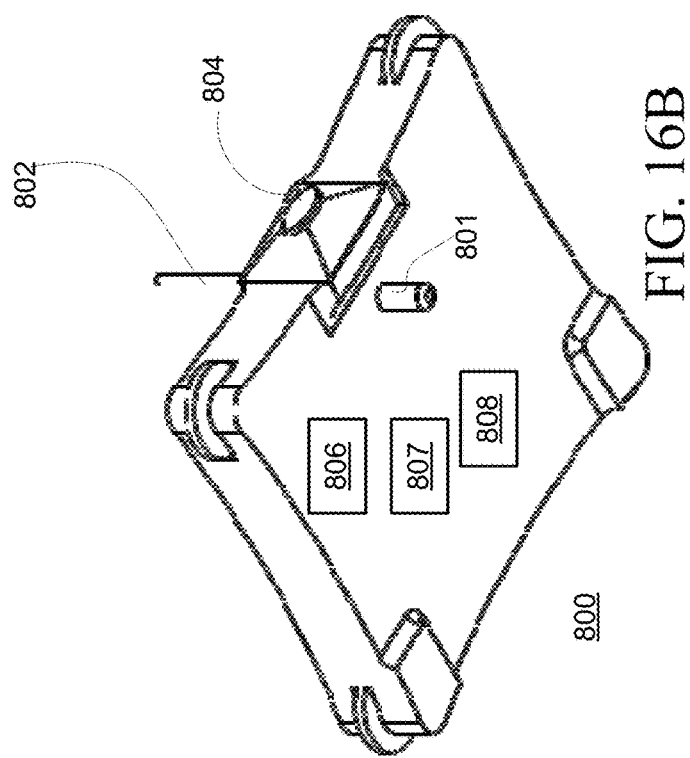

FIGS. 16A and 16B illustrate motorized skimmer 800 (also referred to as waterline leaves and debris partly submerged motorized skimming pool cleaning robot) that performs almost as a fully submerged pool cleaner besides that it will not reach or clean pool floor or wall surfaces. The motorized skimmer 800 includes a spectroscopic device 810 that extends from the bottom of the motorized skimmer (although the spectroscopic device may be positioned elsewhere), a communication module 804, solar panels 805, controller 806, motorized propulsion means such as a motor that sucks fluid and outputs water jets (from openings 803 and/or 804) thereby moving the motorized skimmer, a debris collecting basket (has opening 803) and is located within the motorized skimmer, navigation system 807 and the like.

The solar panels may be used to convert solar energy to power that may be fed to rechargeable battery 808. The rechargeable battery may be fed by other energy sources by using contact and/or contactless charging elements.

The spectroscopic device 801 may be attached to and/or embedded within a waterline motorized skimmer such as the Solar Breeze of solar pool technologies Inc. of Tempa Ariz.

Figure 17:
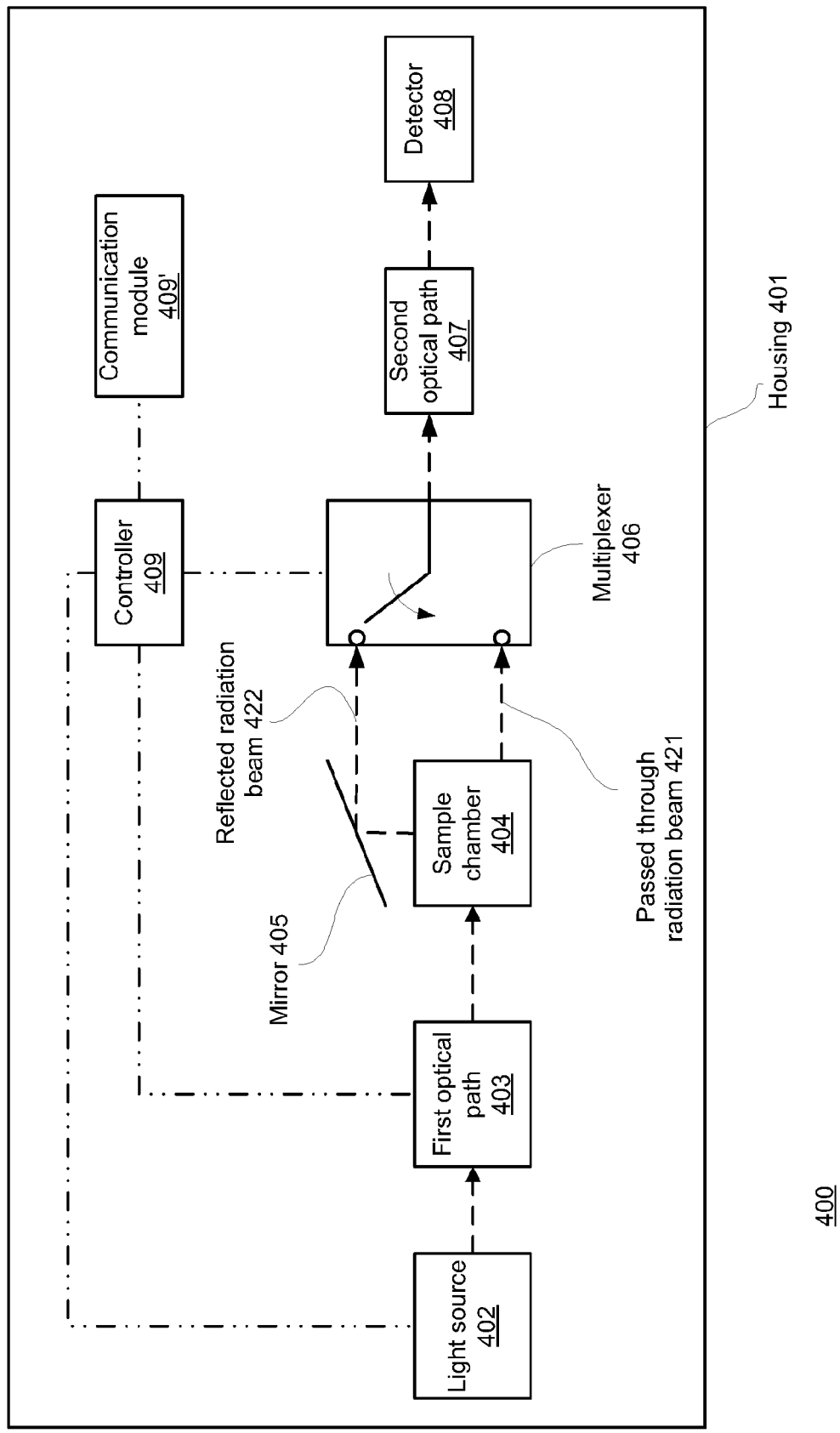
FIG. 17 illustrates a spectroscopic device according to an embodiment of the invention.
Figure 18:
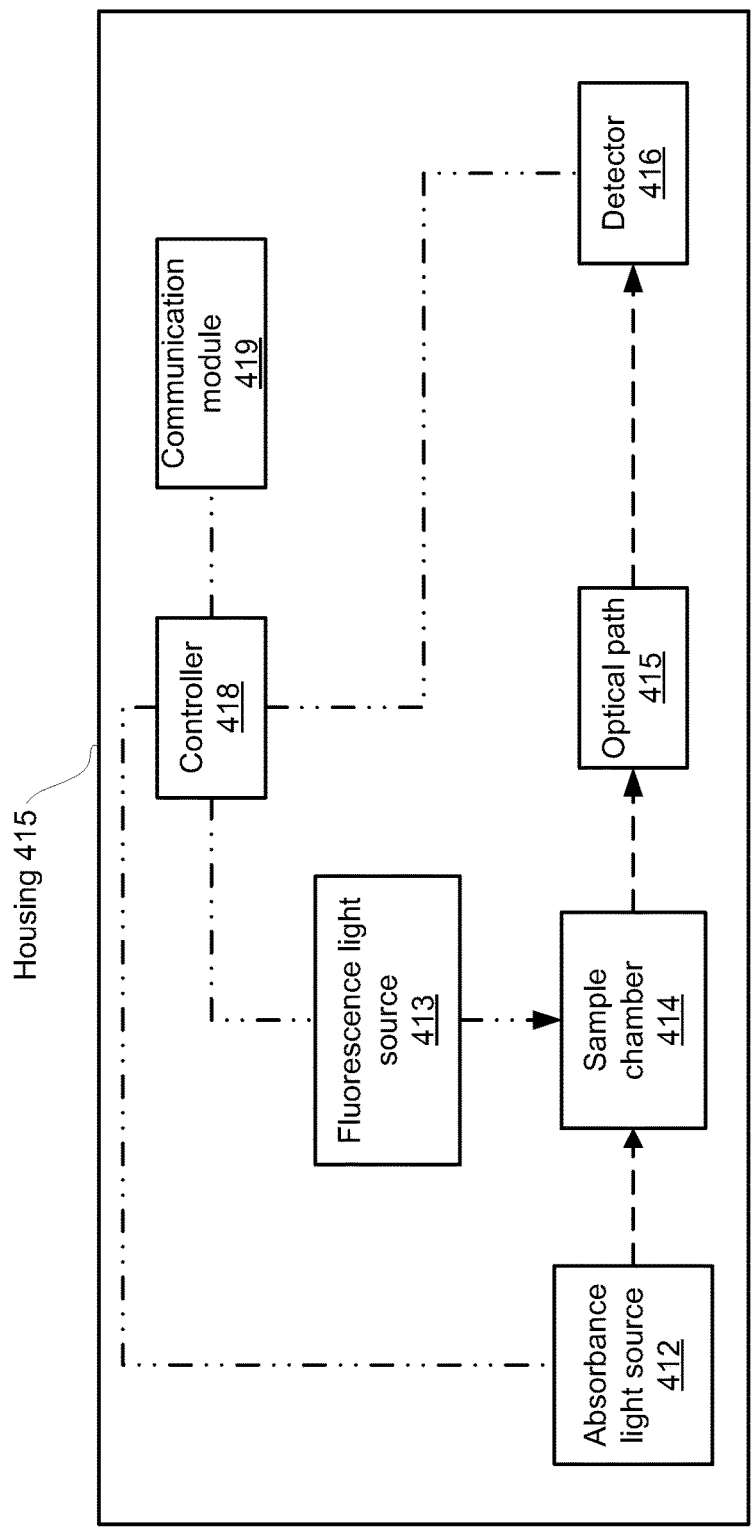
FIG. 18 illustrates a spectroscopic device according to an embodiment of the invention.
Figure 19:
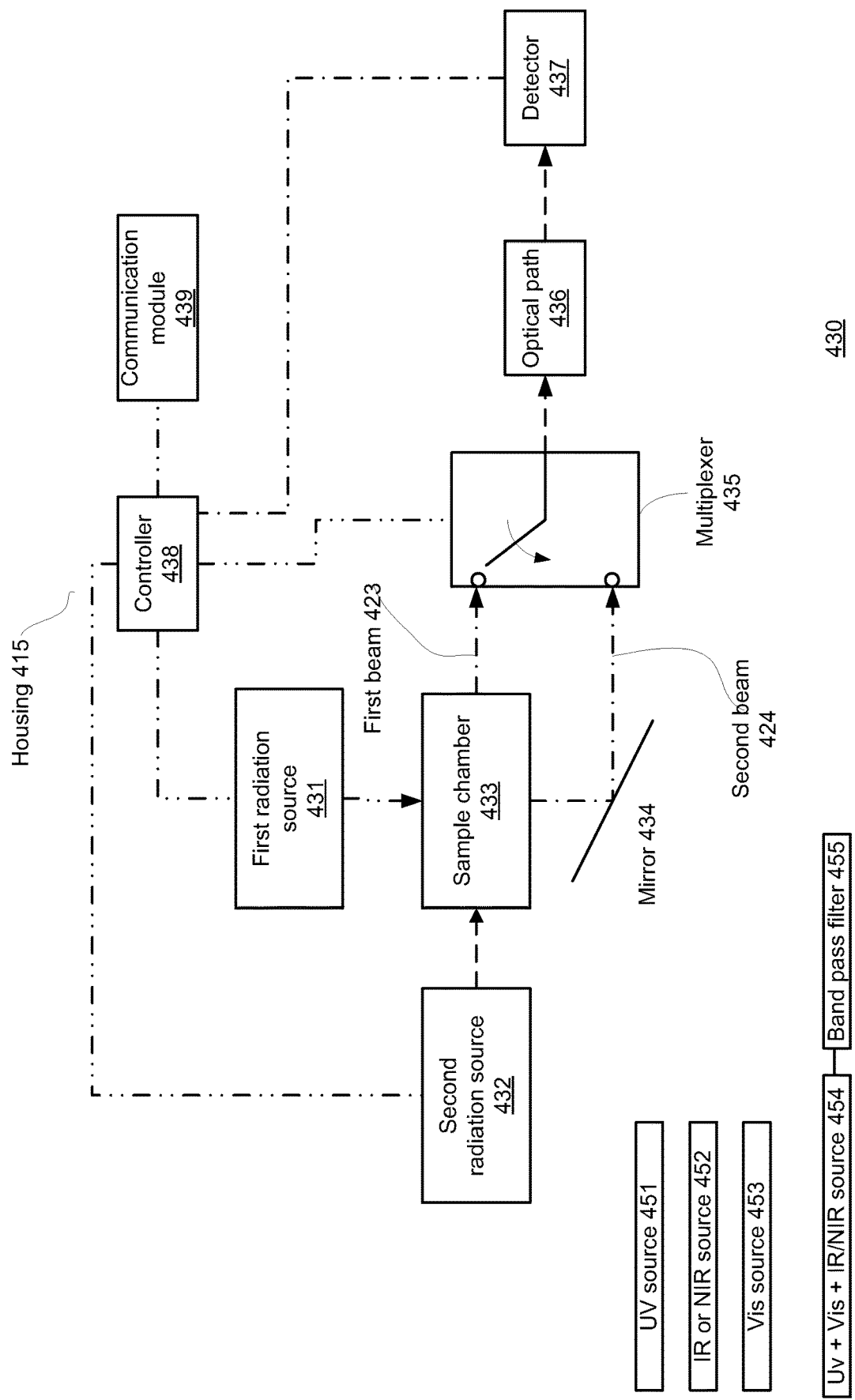
FIG. 19 illustrates a spectroscopic device according to an embodiment of the invention.

The spectroscopic devices 400, 410 and 430 of FIGS. 17, 18 and 19 may be capable of measuring both, fluorescence and absorbance spectra. The spectroscopic device has sufficient sensitivity, sufficient resolution, sufficient signal to noise ratio (SNR) and sufficient dynamic range.

Each one of spectroscopic devices 400, 410 and 430 may include illumination system utilizes low cost LED's, low-cost plastic lenses, low cost plastic filters and low cost glass mirror reflectors for the emission of light. Images are collected on a low cost detector. Many "fingerprints" (Unique spectra of relevant materials detected in two methods: fluorescence and absorbance) were found and accordingly the system has been designed not to cover all the wave length range but to cover all the relevant wave length regions.

Each one of spectroscopic devices 400, 410 and 430 may include LED's or fiber optics that may operate in either one (or combination of) three spectroscopic analysis modes: UVS+VIS+NIR to illuminate the liquid sample from three perpendicular angels at different times.

Each radiation source (or light source) of each one of the spectroscopic devices 400, 410 and 430 may include one or more narrow radiation sources (which may be more energy efficient than a wideband source) such as UV source, IR or NIR source and visual light source (denoted 451, 452 and 453 respectively in FIG. 19), or a wideband source capable of emitting a radiation beam that spans across the UV, visual and IR or NIR ranges (see UV+Vis+IR/NIR source 454 of FIG. 19) that is followed by a band pass filter 455 for outputting the required (one or more) frequency range. A radiation source may be a double-wavelength range light source that may emit radiation in two ranges out of UV, visual and IR or NIR ranges or may include a light source that may emit any radiation beam within the frequency (or wavelength) ranges specified in this specification.

The employment of the above three analysis modes may be simultaneous or cumulative whereby each analysis may be performed separately, when required, one after the other.

Referring to FIG. 17—spectroscopic device 400 includes a radiation source such as light source 402, first optical path 403, sample chamber 404, mirror 405, multiplexer 406, second optical path 407, detector 408, controller 409 and communication module 409'.

Light source 402 may be configured to generate a radiation beam at any desired frequency range (for example UV, visual, IR or near IR) and direct the radiation beam to first optical path 403 that may include any optical components such as beam shapers, filters, lenses, and the like.

The radiation beam impinges on the fluid within the sample chamber 404 thereby causing a passed through radiation beam 421 to pass through the sample chamber and be directed to an input of multiplexer 406 while a reflected radiation beam (also referred to as a fluorescence radiation beam 422 to be reflected towards mirror 405 and to be reflected towards another input of multiplexer 406. Multiplexer 406 may select which beam to send towards detector 408 via the second optical path 407.

The detection signals of the detector 408 may be processed by controller 409, by a processor (not shown) or by the detector itself. The processing may include determining any parameter related to the fluid.

Controller 409 may control the operation of spectroscopic device 400 and communication module 409' may transmit analysis results to the pool maintenance system and/or outside the pool maintenance system.

Housing 401 may be water proof. It is noted that different components of the spectroscopic device 400 may be located in different housings. For example—the detector 408 may be located within a detector housing and may be coupled via optical fibers and/or communication links to other components of the spectroscopic device 400—such as the second optical path and/or to the controller.

Referring to FIG. 18—spectroscopic device 410 includes an absorbance light source 412, a fluorescence light source 413, sample chamber 414, optical path 415, detector 416, controller 418 and communication module 419.

The optical axes of the absorbance light source 412 and the fluorescence light source 413 are normal to each other (or oriented to each other in any other manner).

The absorbance light source 412 has an optical axis that coincides with the optical axis of the optical path 415 thereby a radiation beam sent by the absorbance light source 412 passes through the fluid within the sample chamber 414 and is collected by the optical path 415.

The fluorescence light source 413 has an optical axis that coincides with the optical axis of the optical path 415 thereby a radiation beam sent by the fluorescence light source 413 is reflected from the fluid within the sample chamber 414 and is collected by the optical path 415.

The detection signals of the detector 416 may be processed by controller 418, by a processor (not shown) or by the detector itself. The processing may include determining any parameter related to the fluid.

Controller 418 may control the operation of spectroscopic device 410 and communication module 419 may transmit analysis results to the pool maintenance system and/or outside the pool maintenance system.

Housing 415' may be water proof. It is noted that different components of the spectroscopic device 410 may be located in different housings. For example—the detector 416 may be located within a detector housing and may be coupled via optical fibers and/or communication links to other components of the spectroscopic device 400—such as the second optical path and/or to the controller.

Referring to FIG. 19—spectroscopic device 430 includes first radiation source 431, second radiation source 432, sample chamber 433, mirror 434, multiplexer 435, optical path 436, detector 437, controller 438 and communication module 439.

A radiation beam transmitted by first radiation source 431 may be reflected from the sample chamber 433 to provide a first beam 423 (a fluorescence beam) that is received by a first input of multiplexer 435. The radiation beam may pass through the fluid within sample chamber to be reflected by mirror 434 to provide a second beam 424 (pass through beam) that is received by a second input of multiplexer 435.

A radiation beam transmitted by second radiation source 432 may be reflected from the sample chamber 433 to provide first beam 423 (a pass through beam) that is received by a second input of multiplexer 435. The radiation beam may be reflected from the fluid within sample chamber to be reflected by mirror 434 to provide a second beam 424 (a florescence beam) that is received by a second input of multiplexer 435.

The first and second radiation source may operate simultaneously, at different points of time, at the same wavelength, at different wavelengths and the like.

Each one of the first radiation source 431 and the second radiation source 432 may operate in one or more ranges such as a visible wavelength range, an ultra violet range and an infrared related range (IR or NIR) simultaneously or at different points in time.

When the first and second radiation sources operate simultaneously and at different wavelengths each input of the multiplexer may receive wavelength distinctive pass through beam and a florescence beam thereby increasing a throughput of the spectroscopic device 430.

When either one of spectroscopic devices 400, 410 and 430 performs separate analyses using two of three spectroscopic analysis modes of the following UVS, VIS, NIR modes, the shift from one analysis mode to another may be fully automatic (controlled by a controller of the spectroscopic device or of the pool maintenance system) or initiated by a remote control override.

The automatic shift may involve usage of common internal spectrometer utilities such as a dimmer, a servo motor to shift the angles of the lens or lenses as required.

The spectroscopic device may be waterproof or at least positioned within a waterproof housing.

UV-VIS-NIR hand held spectroscopic devices such as but not limited to spectroscopic devices of Shimadzu Corporation (or affiliates) from Kyoto, Japan and/or Ocean Optics, Inc. from Florida, USA can be used within the pool maintenance systems—especially when the devices are positioned within waterproof housings.

Another, important characteristic may be the wireless communication module that transmits in real time data concerning the levels of organic and inorganic compounds in pools.

Any one of spectroscopic devices 400, 410 and 430 can be either waterproof or be included in a waterproof housing thereby allowing pool water analysis while submerged.

The spectroscopic device may be included within a pool maintenance system and/or may be removably or non-removably attached to the pool maintenance system.

For example, when the pool maintenance system is a pool cleaning robot then the spectroscopic device may be removable attached in the front section with 3 apertures from the device pointing to the pool water. Another embodiment will have it connected in a corner inside the lower section of the housing (in or out of the Motor Unit) with the three apertures connected to holes in the housing.

In "Vis/NIR spectroscopy and chemometrics for the prediction of soluble solids content and acidity (pH) OF KIWI-FRUIT" Ali Moghimi, Mohammad H Aghkhani, Ameneh Sazgarinia and Majid Sarmad, Biosystems Engineering 106 (2010) pages 295-302 it was shown that Visible and near infrared spectroscopic (UV-Vis/NIRS) techniques combined with chemometrics have shown promise as rapid and non-destructive tools to evaluate the various quality attributes of fruits and vegetables. The inventors found that a combination of Visible and near infrared spectroscopic techniques combined with chemometrics are applicable to the analysis of the fluid of pool water.

Figure 20:
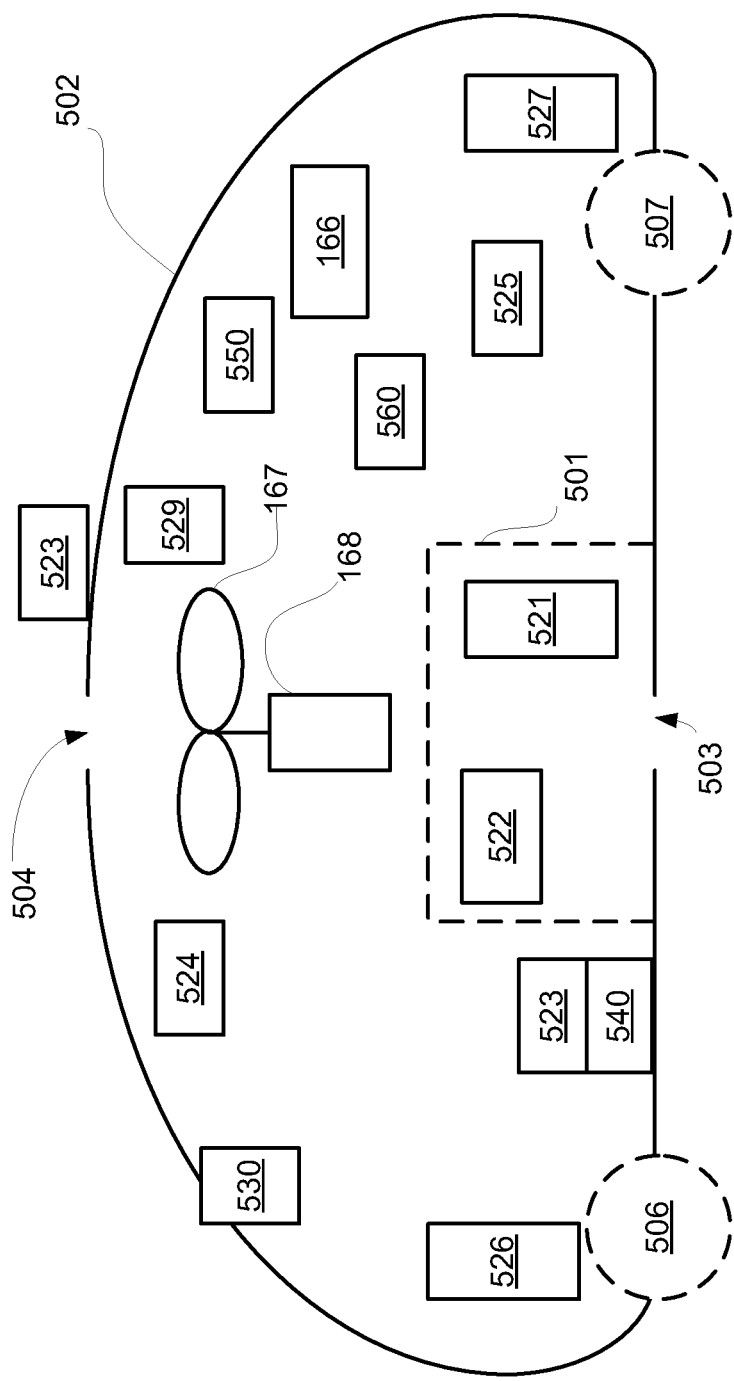
FIG. 20 illustrates a pool cleaning robot according to an embodiment of the invention.

FIG. 20 illustrates a pool cleaning robot 500 that include housing 502, openings 503 and 504, filtering unit 501, impeller 167, pump motor 168 for rotating the impeller, communication module 550, controller 166, an additional sensor 560 and multiple spectroscopic devices 521, 522, 523, 524, 525, 526, 526, 527, 528, 529 and 530.

A single pool cleaning robot 500 may include one, two, three, four, five, six, seven, eight, nine, ten or eleven spectroscopic devices out of multiple spectroscopic devices 521, 522, 523, 524, 525, 526, 526, 527, 528, 529 and 530.

The multiple spectroscopic devices 521, 522, 523, 524, 525, 526, 526, 527, 528, 529 and 530 includes vertically oriented spectroscopic devices (521, 526, 527, 529, 530), horizontally oriented spectroscopic devices (522, 523, 524, 525, 523), spectroscopic devices (521 and 522) that are positioned within the filtering unit, spectroscopic devices (523, 525, 526 and 527) that are near the bottom of the housing, spectroscopic devices (523, 524, 529 and 530) that are located above or at the same height as the impeller, a spectroscopic device 523 that is positioned outside the housing 502, a spectroscopic device 530 that is only partially positioned outside the housing 502.

Any spectroscopic device may be positioned at any orientation and/or any location within the pool cleaning robot.

Any spectroscopic device may be connected to a part or component of the pool cleaning robot by a shock absorber such as shock absorber 540 that is connected to spectroscopic device 523. Any shock absorber known in the art may be used.

Any spectroscopic device be fixed in relation to the housing or may be allowed to move (for example rotate and/or slide) in relation to the housing. For example—a spectroscopic device may rotate about an axis or otherwise rotate in order to maintain the absolute orientation of the fluid chamber regardless of the movement of the pool cleaning robot.

The additional sensor 560 may be used to analyze the fluid of the pool—using an analysis that is not a spectroscopic analysis. Additionally or alternatively, the additional sensor may sense the state of the pool cleaning robot (such as speed of rotation, vibrations, acceleration, orientation of the pool cleaning robot and the like).

The controller 166 may control the operation of the pool cleaning robot (movement, execution of an analysis of the fluid of the pool cleaning robot) based on detection signals from the additional sensor and/or based on an analysis result provided by the spectroscopic device.

For example, if a sequence of analyses results indicates that the fluid deteriorates then the controller 166 may schedule more frequency analyses and/or may generate more frequent or higher priority alerts.

Figure 21:
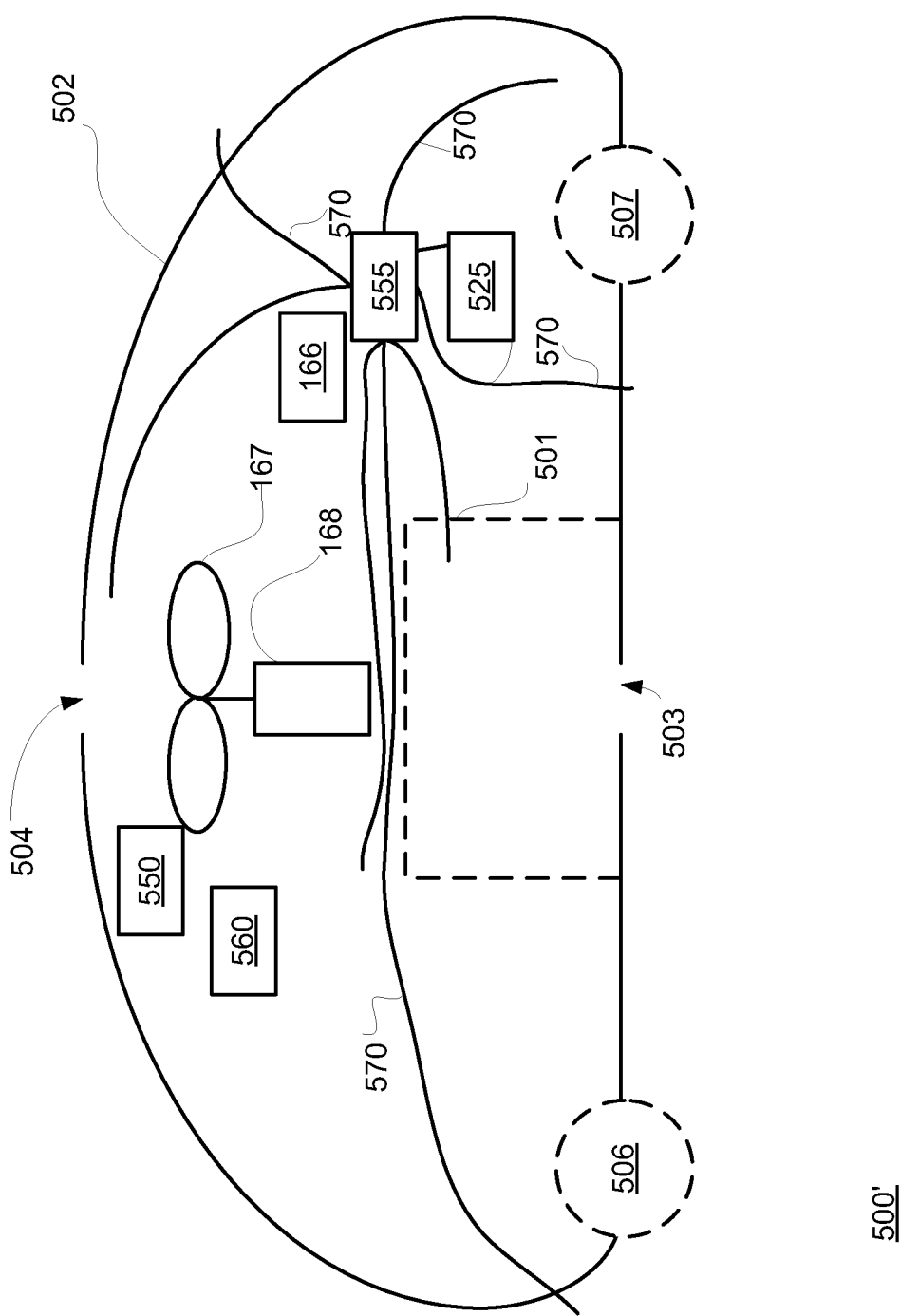
FIG. 21 illustrates a pool cleaning robot according to an embodiment of the invention.

FIG. 21 illustrates a pool cleaning robot 500' that include housing 502, openings 503 and 504, filtering unit 501, impeller 167, pump motor 168 for rotating the impeller, communication module 550, controller 166, additional sensor 560, spectroscopic device 525, fluid conduits 570 and selection unit 555.

Conduits 570 may provide fluid from different sampling points within and/or outside the housing 502. The sampling point may sample fluid within filtering unit 501 or outside the fluid unit 501 (from the bottom and/or rear and/or top and/or front of the housing, near the impeller or far away from the impeller.

The selection unit 555 may be configured to select which conduit will provide the fluid that will be analyzed during a certain analysis. For example—when the pool cleaning robot cleans the bottom of the pool it may be beneficial to sample fluid from the top or the front of the housing (even outside the housing)—as the fluid is cleaner than the fluid sampled at the bottom of the pool cleaning robot. Yet for another example—different orientations of the pool cleaning robot may require sampling from locations that are underwater. Waterline movement of the pool cleaning robot may require sampling from the submerged portion of the pool cleaning robot.

Figure 22:
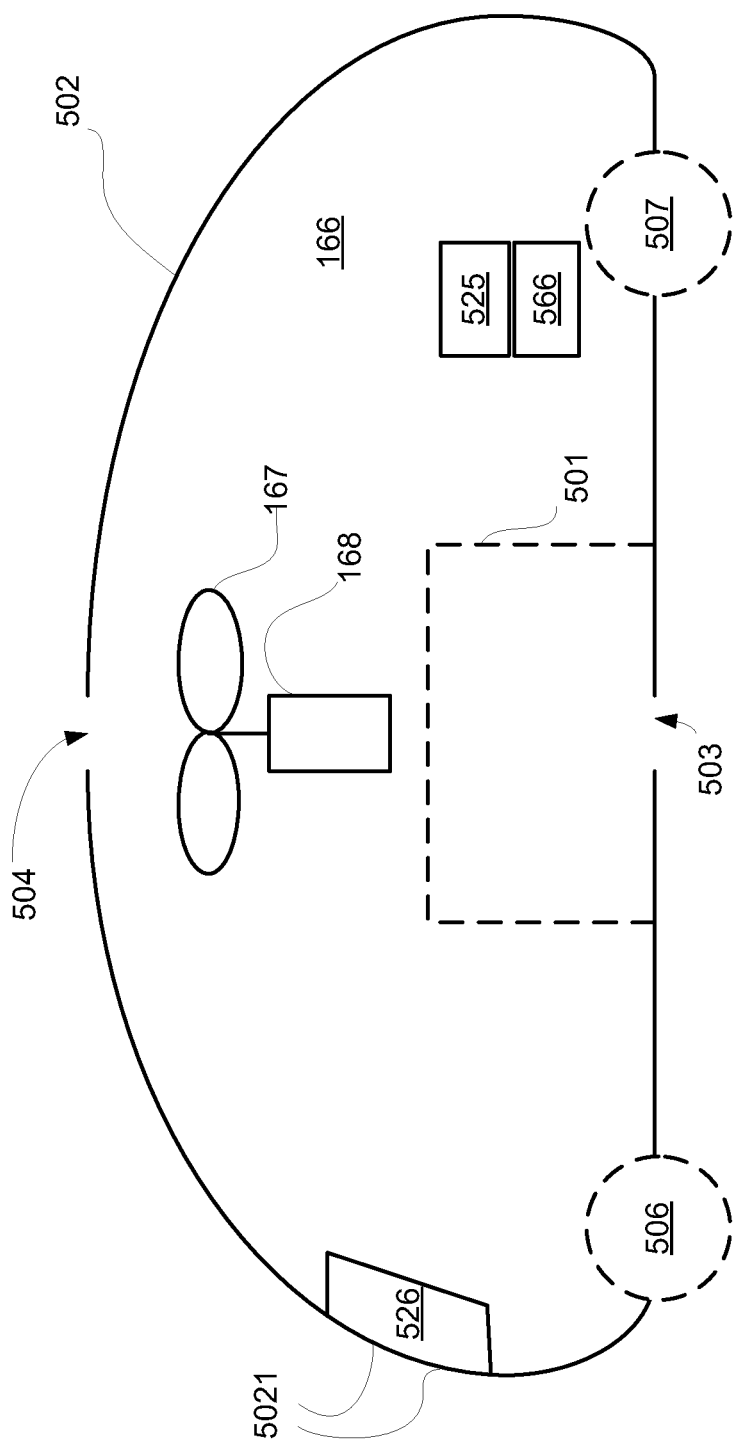
FIG. 22 illustrates a pool cleaning robot according to an embodiment of the invention.

FIG. 22 illustrates a pool cleaning robot 500" that includes housing 502, openings 503 and 504, filtering unit 501, impeller 167, pump motor 168 for rotating the impeller, communication module (not shown), controller (not shown), spectroscopic device 525 that is thermally coupled to a fluid based cooling unit 566 and spectroscopic device 526 that is thermally coupled to a thermally conductive region 5021 of housing 502.

The cooling of the spectroscopic devices (and especially the detector of the spectroscopic device) may increase the signal to noise ratio—and using fluids for cooling may save using a dedicated non-fluid based cooling unit.

Figure 23:
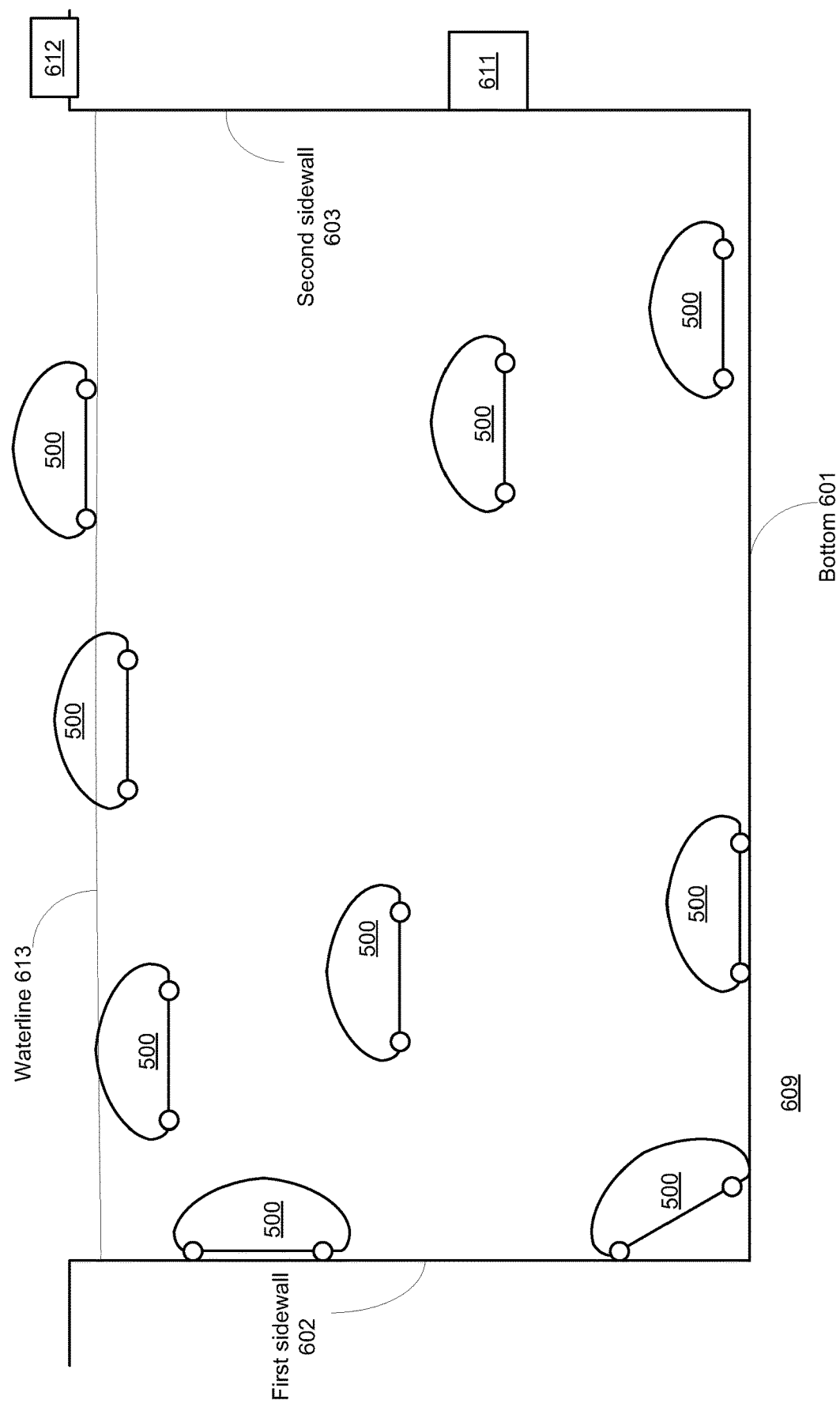
FIG. 23 illustrates a pool, communication modules and a pool cleaning robot according to an embodiment of the invention.

FIG. 23 illustrates a pool 609 that include bottom 601, first and second sidewalls 602 and 603, fluid that reaches a waterline 613, submerged communication module 610, out-of-water communication module 612 and different location of the pool cleaning robot 500 within the pool 609.

The pool cleaning robot may be positioned at different orientations when approaching different locations. The pool cleaning robot may perform different analyses of the fluid of the pool when positioned at one or more locations.

The pool cleaning robot may communicate with submerged communication module 611 and/or an out-of-water communication module 612 that may be a power supply tethered to the pool cleaner via an electrical cable (not shown).

Figure 24:
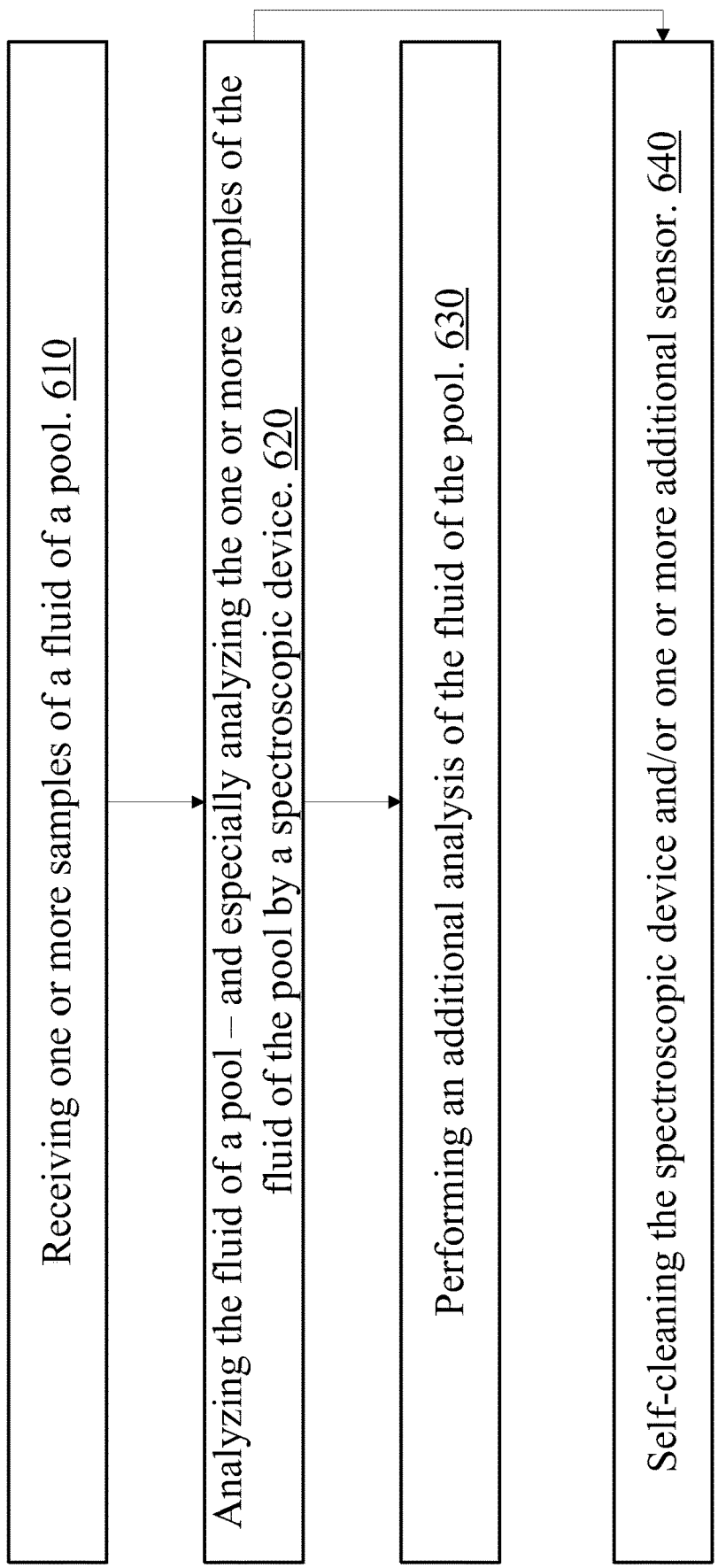
FIG. 24 illustrates a method according to an embodiment of the invention.

FIG. 24 illustrates method 600 that may be executed by any system illustrated above.

The system may be a pool maintenance system such as but not limited to a pool cleaning robot, a skimmer, a pool maintenance system that is coupled to a pool filtering system, a pool maintenance system that is included in a pool filtering system, a pool maintenance system that is mechanically coupled to the pool, a submerged surface skimming pool maintenance system that differs from a pool cleaning robot, and a pool maintenance system that is at least partially submerged in the fluid of the pool when the pool is at least partially filled with the fluid of the pool.

The surface skimmer in FIG. 16, may be a motorized leaves collecting skimmer that may float and propagate (using a motor) above the water—or only partially submerged. It may contain solar panels, a navigation propulsion system, a debris collecting basket, rechargeable batteries, inductive or wired battery recharging element, bumpers or bumper wheels, electronic control box with or without wireless communications.

Method 600 may include step 610 of receiving one or more samples of a fluid of a pool. The samples may be received within a sample chamber. The fluid within the sample chamber may captured within the sample chamber of may flow through the sample chamber during step 620.

The fluid may be captured by using valves or any other fluid control elements. The sample chamber may be of any shape (circular, have flat facets) and size. For example—the sample chamber may be a part of a fluid conduit—such as a pipe.

The samples may be received only when preparing to perform an analysis of the fluid or may be executed regardless of the timing of the analysis (for example the fluid may pass through the sample chamber even before the analysis takes place).

Step 610 may be followed by step 620 of analyzing the fluid of a pool—and especially analyzing the one or more samples of the fluid of the pool by a spectroscopic device.

Step 620 may include applying any number of spectroscopic techniques out of: (a) ultra-violet-visible spectroscopy, (b) absorbance ultra-violet-visible spectroscopy, (c) fluorescence ultra-violet-visible spectroscopy, (d) near infrared spectroscopy, (e) absorbance near infrared spectroscopy, (f) fluorescence near infrared spectroscopy, and (g) synchronous fluorescence spectroscopy, (h) reflectance ultra-violet-visible spectroscopy.

Step 620 may include applying a chemometric algorithm.

Step 620 may include analyzing at least two of the following: (a) a wavelength range between one hundred eighty nanometers and two hundred nanometers, (b) one or more sub-region of a wavelength range between one hundred eighty nanometers and two hundred nanometers, (c) a wavelength range between two hundred and sixty nanometers and two hundred and eighty nanometers, (d) one or more sub-region of a wavelength range between two hundred and sixty nanometers and two hundred and eighty nanometers, (e) a wavelength of two hundred and fifty four nanometers, (f) a wavelength range between nine hundred eighty nanometers and one thousand nanometers, (g) one or more sub-region of a wavelength range between nine hundred eighty nanometers and one thousand nanometers, (h) a wavelength range between one thousand two hundred and sixty nanometers and one thousand two hundred and eighty nanometers, (i) one or more sub-region of a wavelength range between one thousand two hundred and sixty nanometers and one thousand two hundred and eighty nanometers, and (j) a wavelength of one thousand two hundred and fifty four nanometers.

Step 620 may include applying the one or more spectroscopic technique at a resolution of one nanometer, or a resolution that does not exceed one nanometer or a resolution that exceeds one nanometer.

Step 620 may include directing, by optics, electromagnetic radiation through an opening formed in a pipe and receiving electromagnetic radiation from the fluid.

Step 620 may include at least one of the following:
a. Illuminating by multiple radiation sources a sample of the fluid of the pool with multiple radiation beams from different directions; directing, by collection optics, to at least one sensor, one or more radiation beams out of a passed through radiation beam that passes through the sample and a reflected radiation beam that was reflected from the sample.
b. Directing by the collection optics, to the at least one sensor, the passed through radiation beam and the reflected radiation beam at the same point in time.
c. Directing by the collection optics, to the at least one sensor, the passed through radiation beam and the reflected radiation beam at different points in time.
d. Directing, by the collection optics, to a first sensor of the at least one sensor the passed through radiation beam; and directing to a second sensor of the at least one sensor the reflected radiation beam.
e. Illuminating, by the multiple radiation sources, the sample with the multiple radiation beams at different points of time.
f. Illuminating, by the multiple radiation sources, the sample with the multiple radiation beams simultaneously.

The multiple radiation sources may include at least two radiation sources out of an ultraviolet source, a visible light source and a near infrared source.

The multiple radiation sources may include an ultraviolet source, a visible light source and a near infrared source.

The multiple radiation sources may include a dual frequency range radiation source and single radiation range radiation source. A dual frequency radiation source is configured to generate radiation within two frequency ranges out of ultraviolet, near infrared and visible light. A single radiation range radiation source is configured to generate radiation within a single frequency range out of ultraviolet, near infrared and visible light.

The multiple radiation sources may include a first dual frequency range radiation source that has a first optical axis and a second dual frequency radiation range source that has a second optical axis. The first and second optical axes may be oriented to each other. Each dual frequency radiation source may be configured to generate radiation within two frequency ranges out of ultraviolet, near infrared and visible light.

Step 620 may include generating, by the first and second dual frequency range radiation sources, at a same point of time, radiation beams that differ from each other by frequency.

Step 620 may include directing, at a first point in time and by the collection optics, towards the at least one sensor a passed through radiation beam of a first frequency range that passes through the sample and a reflected radiation beam of a second radiation range that was reflected from the sample.

Step 620 may include illuminating, by a single radiation source, a sample of the fluid of the pool with a radiation beam; directing, by collection optics and to the at least one sensor, one or more radiation beams out of a passed through radiation beam that passes through the sample and a reflected radiation beam that was reflected from the sample.

Step 620 may include determining, automatically and by a controller of the pool maintenance system, when to apply fluorescence spectroscopy and when to apply absorbance spectroscopy. The determination may be made based on a predefined schedule, may be determined randomly, may be determined based on previous analyses of the fluid of the pool, and the like.

Step 620 may be executed by a spectroscopic device that is waterproof. It may include at least a portion that contacts the fluid of the pool. The sample chamber may be regarded as a part of the spectroscopic device.

Step 620 may include analyzing the fluid of the pool to provide information about levels of organic and inorganic materials in the pool.

Step 620 may include selecting, out of multiple fluid conduits for receiving the fluid of the pool from multiple locations, a selecting a selected conduit for providing the fluid to the spectroscopic device for a given analysis. The selection may change from one analysis to the other.

Method 600 may include step 630 of performing an additional analysis of the fluid of the pool. The analysis can be performed on the sampled obtained during step 610 or on other samples. The additional analysis is not a spectroscopic analysis.

Step 630 may include performing the additional analysis by at least one additional sensor out of (a) a pH sensor, (b) a ORP sensor, (c) a temperature sensor, (d) an electrical conductivity sensor, (e) a pressure sensor, (f) ion-selective electrodes, (g) a flow rate sensor, (h) a free Chlorine sensor, (i) a combined Chlorine sensor, (j) a turbidity sensor, (k) a Cyanuric sensor, (l) an Alkalinity sensor, (m) a Salinity sensor.

Method 600 may also include step 640 of self-cleaning the spectroscopic device and/or one or more additional sensor. Self-cleaning refers to cleaning by the system and not by a human.

The self-cleaning may involve using a self-cleaning mechanism such as but not limited to an acoustic vibrator, a mechanical cleaning element.

Either one of steps 610, 620, 630 and 640 can be executed by a pool cleaning robot, by a system that includes a floating unit and a submerged unit, by a system that is connected to the sidewall of the pool, by a skimmer, by a system that is included within a skimmer, by a system that receives fluid from a pool filtering system, by the pool filtering system.

Figure 25:
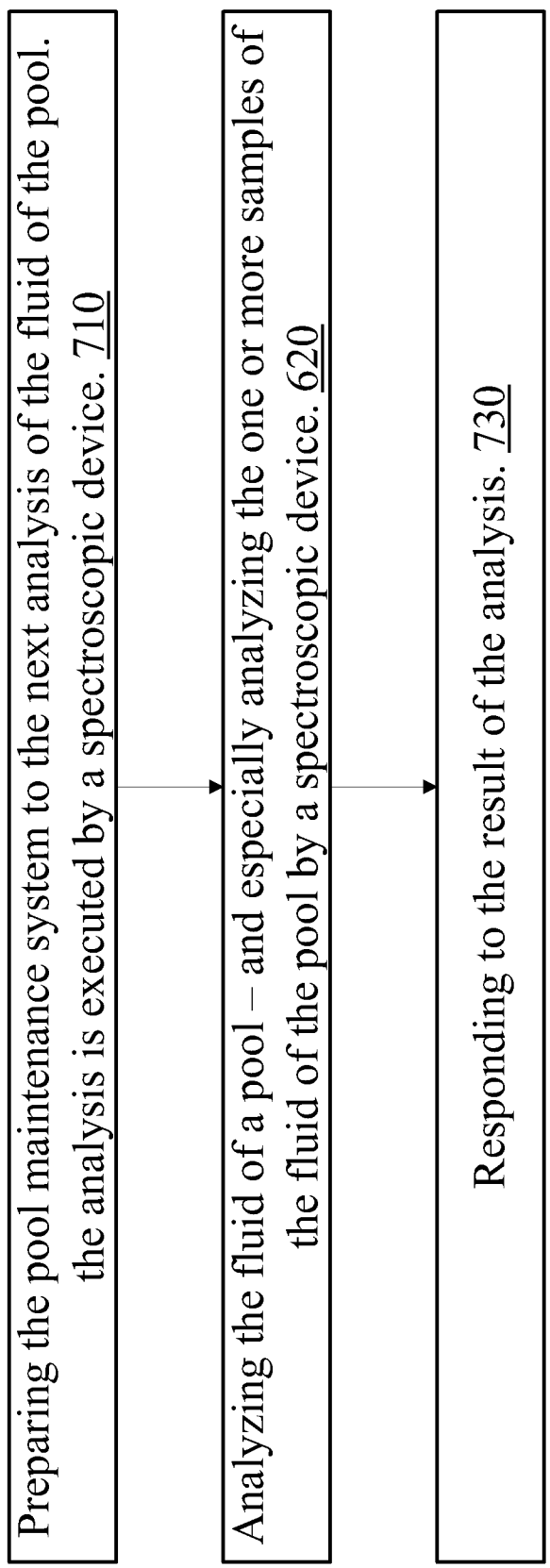
FIG. 25 illustrates a method according to an embodiment of the invention.

FIG. 25 illustrates method 700 that may be executed by any system illustrated above.

Method 700 differs from method 600 by including some additional steps.

Method 700 may start by step 610 and by step 710.

Step 710 may include preparing the pool maintenance system to the next analysis of the fluid of the pool. The analysis is executed by a spectroscopic device.

Step 710 may include step 610.

Step 710 may also include sensing a status of the pool cleaning robot, determining whether the current status facilitates the execution of analysis (of step 620), wherein if the current status does not facilitate the execution of the analysis then either changing the status or determining that the analysis cannot be executed. If the latter occurs the analysis may be postponed, an alert or an indication may be transmitted from the pool cleaning robot, and the like.

Assuming that the status may be modified then step 710 may also include modifying the status.

The status may be a cleanliness of the pool maintenance system (especially of the fluid chamber), the speed of propagation of the pool maintenance system, a velocity of the pool maintenance system, an acceleration of the pool maintenance system and an inclination of the pool maintenance system.

Some pool maintenance system may change all of these parameters while other (for example static pool maintenance systems) may change only some of the parameters.

In some cases, it may be desired to perform the analysis of the fluid of the pool when the pool maintenance system propagates at a velocity that is below a certain speed threshold, when the acceleration of the pool maintenance system is below an acceleration threshold, when the inclination of the pool maintenance system is within a certain range and/or when the pool maintenance system is clean enough.

Any of the above mentioned thresholds may be set (or be taken into account) based on a desired signal to noise ratio (or any other parameter) related to the analysis.

For example—if the spectrum of a certain material or organism of interest includes relatively low peaks (in comparison to another material or organism that has higher peaks) than the signal to noise ratio that should be obtained when looking for the certain material or organism may be higher than the signal to noise ration that should be obtained when the other material is being looked for. Accordingly—the pool maintenance system should be cleaner, propagate slower and/or does not dramatically accelerate when searching for the certain material or organism.

Step 710 may include controlling the movement of the pool maintenance system.

Step 710 may be followed by step 620.

Step 620 may be followed by 730 of responding to the result of the analysis.

Step 730 may include step 630 and/or step 640.

Additionally or alternatively, step 730 may include at least one of the following:
  a. Scheduling the next iteration of steps 710 and 620. The scheduling may be executed in a pseudo-random manner or in a manner that is not random at all.
  b. Scheduling multiple analyses of the fluid of the pool at different locations within the pool. At least two locations of the different locations may be positioned at different distances from a bottom of the pool. One location of the different locations may be at a bottom of the pool and another location of the different positioned may be at a surface of the fluid (waterline). The pool cleaning robot may be positioned at a first orientation when located at a first location of the different locations, and the pool cleaning robot may be positioned at a second orientation when located at a second location of the different locations. The first orientation may differ from the second orientation. The difference may be ninety degrees, above ten degrees, and the like.
  c. Receiving, by the controller, a schedule of multiple analyses of the fluid of the pool and modifying the schedule based on at least one result of at least one analysis of the multiple analyses.
  d. Determining, by the spectroscopic device, a signal to noise ratio of a result of an analysis executed by the spectroscopic device; and determining, by the controller, at least one parameter of a future analysis based on the signal to noise ratio of the result.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements the mere fact that certain measures are recited in mutually different claims does not indicate that a combination of these measures cannot be used to advantage.

Any reference to the term "comprising" or "having" should be interpreted also as referring to "consisting" of "essentially consisting of". For example—a system that comprises certain components can include additional components, can be limited to the certain components or may include additional components that do not materially affect the basic and novel characteristics of the system—respectively.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A pool maintenance system comprising:
   a spectroscopic device; wherein the pool maintenance system is a pool cleaning robot; wherein the spectroscopic device is configured to analyze a fluid of a pool; and
   a controller that is configured to receive a schedule of multiple analyses of the fluid of the pool and modify the schedule based on at least one result of at least one analysis of the multiple analyses.

2. The pool maintenance system according to claim 1 wherein the spectroscopic device is configured to analyze the fluid of the pool by applying fluorescence spectroscopy and absorbance spectroscopy.

3. The pool maintenance system according to claim 2 wherein the spectroscopic device comprises:
   multiple radiation sources for illuminating a sample of the fluid of the pool with multiple radiation beams from different directions;
   at least one sensor; and
   collection optics for directing, to the at least one sensor, one or more radiation beams out of a passed through radiation beam that passes through the sample and a reflected radiation beam that was reflected from the sample.

4. The pool maintenance system according to claim 3 wherein the collection optics is configured to direct to a first sensor of the at least one sensor the passed through radiation beam and to direct to a second sensor of the at least one sensor the reflected radiation beam.

5. The pool maintenance system according to claim 3 wherein the multiple radiation sources comprises a dual frequency range radiation source and single radiation range radiation source; wherein the dual frequency range radiation source is configured to generate radiation within two frequency ranges out of ultraviolet, near infrared and visible light; wherein the single radiation range radiation source is configured to generate radiation within a single frequency range out of ultraviolet, near infrared and visible light.

6. The pool maintenance system according to claim 1, wherein the pool maintenance system is a pool cleaning robot; wherein the pool cleaning robot comprises a sensor for sensing a status of the pool cleaning robot; wherein the controller is configured to control a movement of the pool cleaning robot based on a status of the pool cleaning robot as sensed by the sensor and based on one or more scheduled analysis of the fluid of the pool by the spectroscopic device.

7. The pool maintenance system according to claim 6 wherein the status of the pool cleaning robot is selected out of a speed of propagation of the pool cleaning robot, an inclination of the pool cleaning robot, an acceleration of the pool cleaning robot, and vibrations of the pool cleaning robot.

8. The pool maintenance system according to claim 6, wherein the sensor is a vibration sensor that is configured to sense vibrations of the pool cleaning robot; wherein the controller is configured to facilitate an analysis of the fluid of the pool only when the vibrations of the pool maintenance system is below a vibrations threshold.

9. The pool maintenance system according to claim 6, wherein the sensor is a speed sensor that is configured to sense a speed of propagation of the pool cleaning robot; and wherein the controller is configured to control a reduction of a speed of propagation of pool cleaning robot to be below a speed threshold during an analysis of the fluid of the pool.

10. The pool maintenance system according to claim 6, wherein the sensor is a vibration sensor that is configured to sense vibrations of the pool cleaning robot; and wherein the controller is configured to control a reduction of a vibration of propagation of pool cleaning robot to be below a vibration threshold during an analysis of the fluid of the pool.

11. The pool maintenance system according to claim 1, wherein the controller is configured to schedule the multiple analyses of the fluid of the pool at different locations within the pool.

12. The pool maintenance system according to claim 11, wherein at least two locations of the different locations are positioned at different distances from a bottom of the pool.

13. The pool maintenance system according to claim 11, wherein one location of the different locations is at a bottom of the pool and another location of the different locations is at a surface of the fluid.

14. The pool maintenance system according to claim 1 further comprising a controller; wherein the spectroscopic device is configured to determine a signal to noise ratio of a result of an analysis executed by the spectroscopic device; and wherein the controller is configured to determine at least one parameter of a future analysis based on the signal to noise ratio of the result.

15. The pool maintenance system according to claim 1, wherein the pool maintenance system is a pool cleaning robot that comprises a controller; wherein the spectroscopic device is configured to determine a signal to noise ratio of a result of an analysis executed by the spectroscopic device; and wherein the controller is configured to control a movement of the pool cleaning robot based on the signal to noise ratio of the result and based on one or more scheduled analyses of the fluid of the pool by the spectroscopic device.

16. The pool maintenance system according to claim 1 comprising a cooling unit for cooling a sensor of the spectroscopic device using the fluid of the pool.

17. The pool maintenance system according to claim 1 wherein the pool maintenance system is further configured to control water quality and hygiene parameters of the fluid of the pool.

18. The pool maintenance system according to claim 1 wherein the spectroscopic device is mechanically coupled to a shock absorber.

19. The pool maintenance system according to claim 1 comprising a housing; wherein the housing comprises a thermal conductive region; wherein a sensor of the spectroscopic device is thermally coupled to the thermal conductive region.

20. The pool maintenance system according to claim 1 comprising multiple fluid conduits for receiving the fluid of the pool from multiple locations and a selection unit for selecting a selected conduit for providing the fluid to the spectroscopic device for a given analysis.

21. A pool maintenance system comprising:
    a spectroscopic device; wherein the pool maintenance system is a pool cleaning robot; wherein the spectroscopic device is configured to analyze a fluid of a pool to provide information about levels of organic and inorganic materials in the pool; and
    a controller that is configured to receive a schedule of multiple analyses of the fluid of the pool and modify the schedule based on at least one result of at least one analysis of the multiple analyses.

22. A method for analyzing a fluid of a pool, the method comprises:
    receiving one or more samples of a fluid of a pool;
    analyzing the fluid of the pool, wherein the analyzing comprises using a spectroscopic device associated with a pool maintenance system; and wherein the pool maintenance system is a pool cleaning robot;
    receiving, by a controller of the pool maintenance system, a schedule of multiple analyses of the fluid of the pool; and
    modifying the schedule based on at least one result of at least one analysis of the fluid of the pool.

* * * * *